US011458254B2

(12) United States Patent
Schmid et al.

(10) Patent No.: US 11,458,254 B2
(45) Date of Patent: Oct. 4, 2022

(54) ADJUSTABLE INJECTION DEVICE

(71) Applicant: Ypsomed AG, Burgdorf (CH)

(72) Inventors: Lorenz Schmid, Solothurn (CH); Peter Stettler, Ersigen (CH); Urs Klötzli, Burgdorf (CH); Adrian Eich, Wangenried (CH); Vinzenz Frauchiger, Solothurn (CH)

(73) Assignee: Ypsomed AG, Burgdorf (CH)

( * ) Notice: Subject to any disclaimer, the term of this patent is extended or adjusted under 35 U.S.C. 154(b) by 258 days.

(21) Appl. No.: 16/807,475

(22) Filed: Mar. 3, 2020

(65) Prior Publication Data

US 2020/0197613 A1    Jun. 25, 2020

Related U.S. Application Data

(63) Continuation of application No. 15/810,807, filed on Nov. 13, 2017, now Pat. No. 10,610,646, which is a
(Continued)

(30) Foreign Application Priority Data

May 13, 2015    (CH) .......................................... 667/15

(51) Int. Cl.
*A61M 5/31*     (2006.01)
*A61M 5/32*     (2006.01)
*A61M 5/20*     (2006.01)

(52) U.S. Cl.
CPC ........ *A61M 5/3129* (2013.01); *A61M 5/3204* (2013.01); *A61M 5/326* (2013.01);
(Continued)

(58) Field of Classification Search
CPC .... A61M 2005/2006; A61M 2205/586; A61M 2005/3142
See application file for complete search history.

(56) References Cited

U.S. PATENT DOCUMENTS 6,277,099 B1 *    8/2001  Strowe ................ A61M 5/3158
                                                        604/207
6,589,210 B1      7/2003  Rolfe
(Continued)

FOREIGN PATENT DOCUMENTS

EP      0458366 A2 *   11/1991   ............... G07F 7/06
EP      2335757 A2      6/2011
(Continued)

OTHER PUBLICATIONS

International Preliminary Report on Patentability received for International Application No. PCT/CH2016/000074, dated Nov. 14, 2017, 8 pages.
(Continued)

*Primary Examiner* — William R Carpenter
(74) *Attorney, Agent, or Firm* — Dorsey & Whitney LLP

(57) ABSTRACT

An apparatus and method for adjusting an injection device for administering a substance that includes a device housing with an array of fastening points. The apparatus has at least two housing-like shells, each having at least one holding device and at least one blocking device for attaching to the housing. The holding device of a first shell can be attached to a fastening point, and the holding device of a second shell can be attached to a further fastening point. Upon attaching all of the plurality of housing-like shells to the housing, the blocking devices of the plurality of housing-like shells prevent the disengagement of the plurality of housing-like shells from the housing by blocking detachment of the holding devices from the fastening points. At least one of the housing-like shells comprises an electronic assembly and shell attachment to the housing activates the electronic assembly.

20 Claims, 28 Drawing Sheets

Related U.S. Application Data continuation of application No. PCT/CH2016/000074, filed on May 3, 2016.

(52) U.S. Cl.
CPC ..... *A61M 5/2033* (2013.01); *A61M 2005/208* (2013.01); *A61M 2005/3142* (2013.01); *A61M 2005/3267* (2013.01); *A61M 2205/3368* (2013.01); *A61M 2205/3584* (2013.01); *A61M 2205/50* (2013.01); *A61M 2205/581* (2013.01); *A61M 2205/582* (2013.01); *A61M 2205/586* (2013.01); *A61M 2205/587* (2013.01); *A61M 2205/80* (2013.01); *A61M 2205/8206* (2013.01)

(56) References Cited

U.S. PATENT DOCUMENTS

| | | | |
|---|---|---|---|
| 8,535,274 | B2 | 9/2013 | Genetay et al. |
| 8,708,971 | B2 | 4/2014 | Segal |
| 2003/0050606 | A1 | 3/2003 | Brand et al. |
| 2004/0010233 | A1 | 1/2004 | Hjertman et al. |
| 2005/0020979 | A1 | 1/2005 | Westbye et al. |
| 2009/0157012 | A1 | 6/2009 | Magne |
| 2011/0137281 | A1 | 6/2011 | Tang |
| 2011/0178500 | A1* | 7/2011 | Shang ............... A61M 5/20 604/506 |
| 2011/0218502 | A1* | 9/2011 | Iio ............... A61B 5/150022 320/108 |
| 2011/0257602 | A1* | 10/2011 | Watanabe ............... A61M 5/20 604/189 |
| 2011/0295215 | A1* | 12/2011 | Nielsen ............... G16H 20/17 604/257 |
| 2012/0289905 | A1 | 11/2012 | Julian et al. |
| 2013/0131601 | A1* | 5/2013 | Pommereau ............... A61M 5/3129 604/189 |
| 2017/0007769 | A1 | 1/2017 | Chang et al. |

FOREIGN PATENT DOCUMENTS

| | | | |
|---|---|---|---|
| WO | WO-0207802 A1 * | 1/2002 | ............ A61M 5/344 |
| WO | 03105927 | 12/2003 | |
| WO | WO-2010037828 A1 * | 4/2010 | ............ A61M 5/178 |
| WO | 2011124633 | 10/2011 | |
| WO | 2012127365 | 9/2012 | |
| WO | WO-2013113818 A1 * | 8/2013 | ............ A61M 5/172 |
| WO | 2015078758 | 6/2015 | |
| WO | 2016179713 | 11/2016 | |

OTHER PUBLICATIONS

International Search Report received for International Application No. PCT/CH2016/000074, dated Jun. 23, 2016, 3 pages.

* cited by examiner

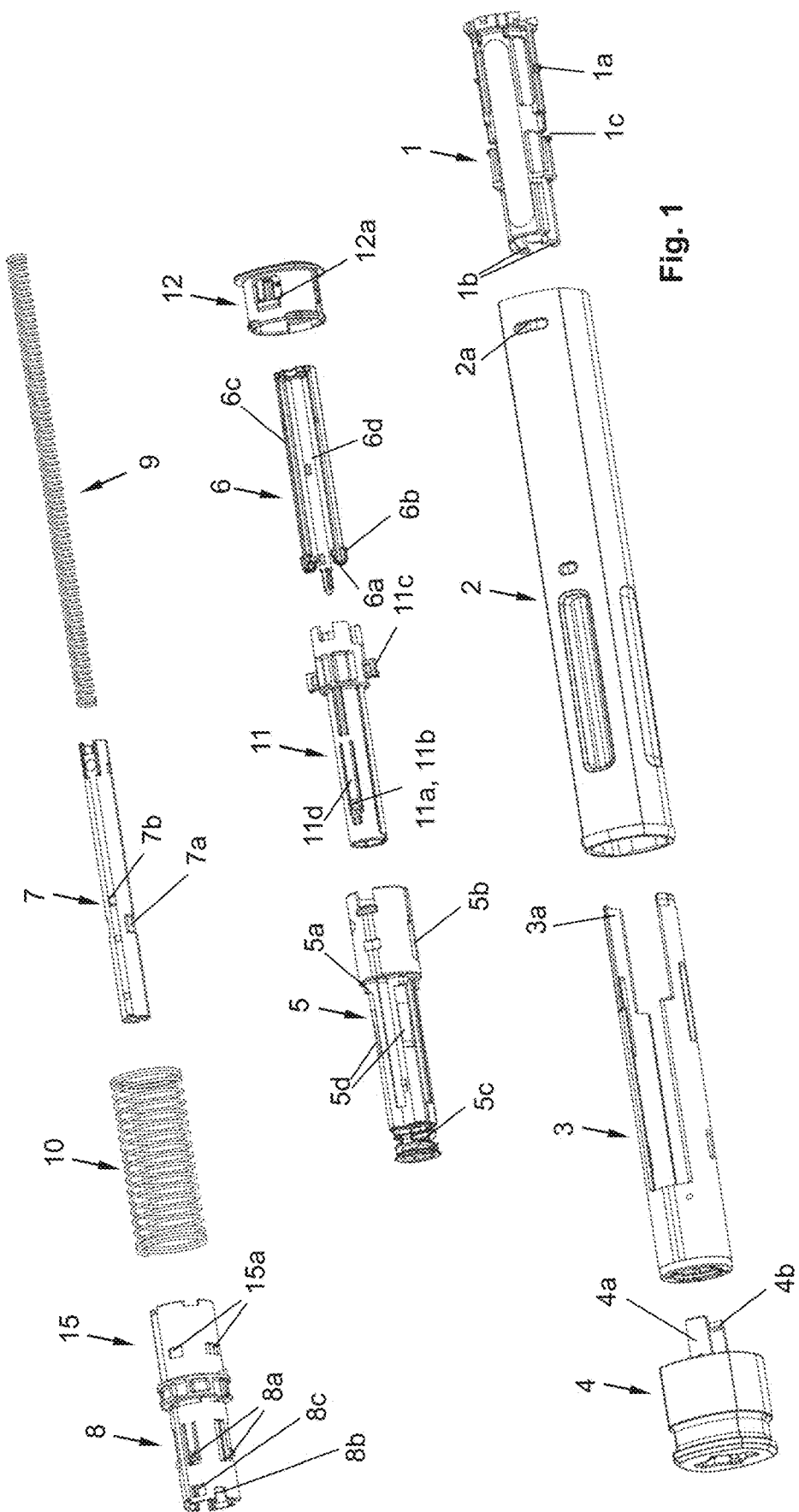

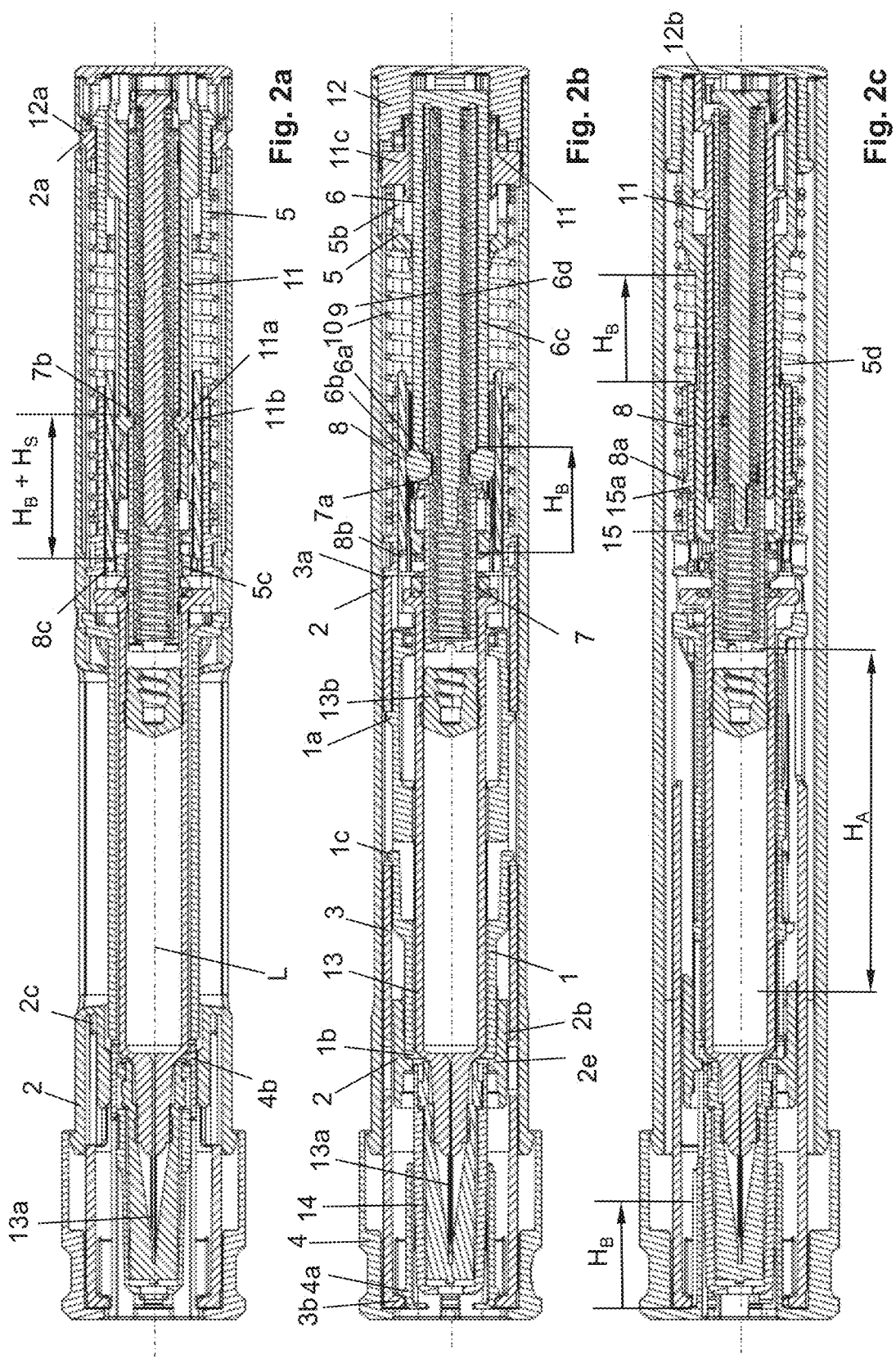

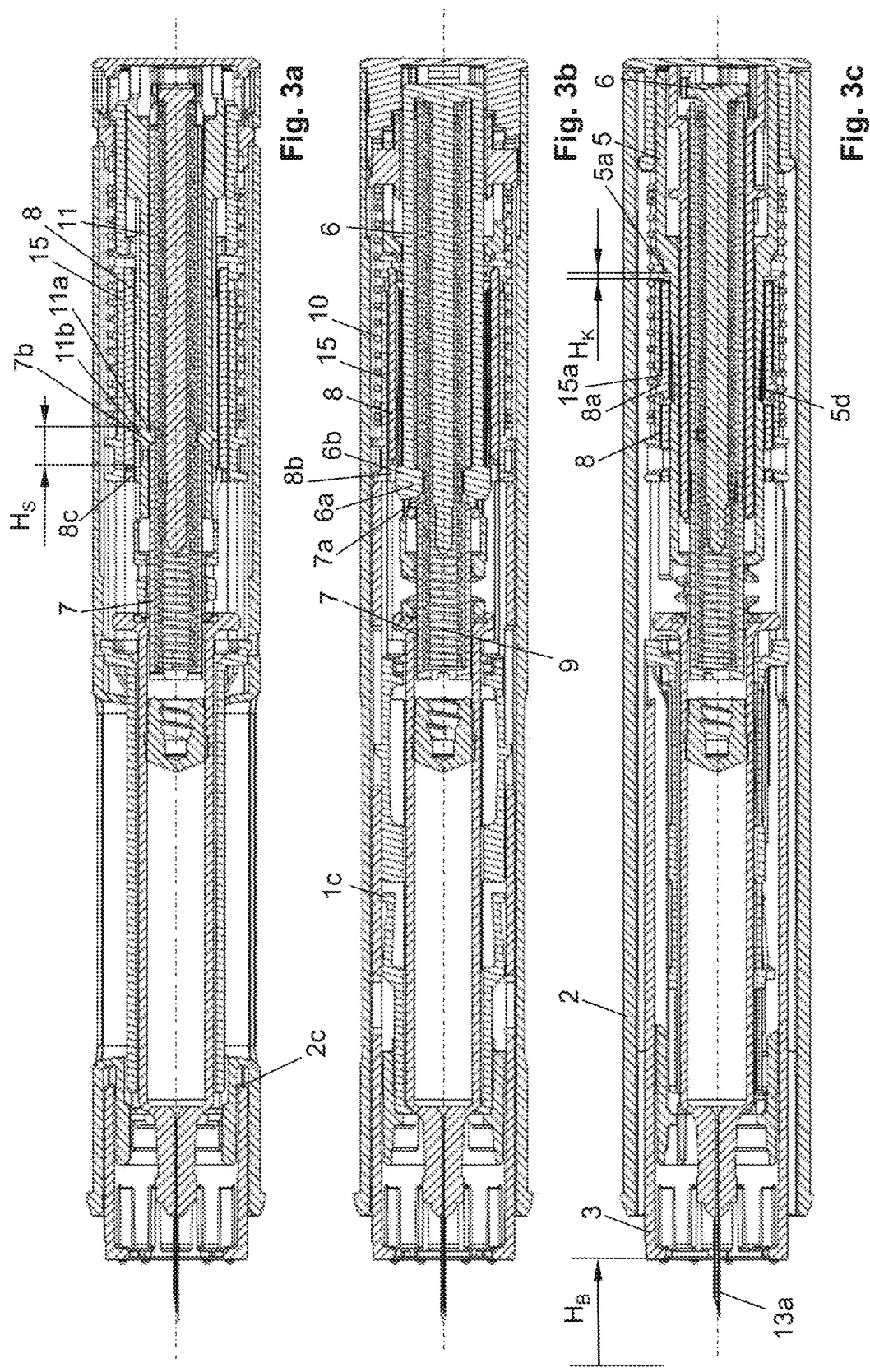

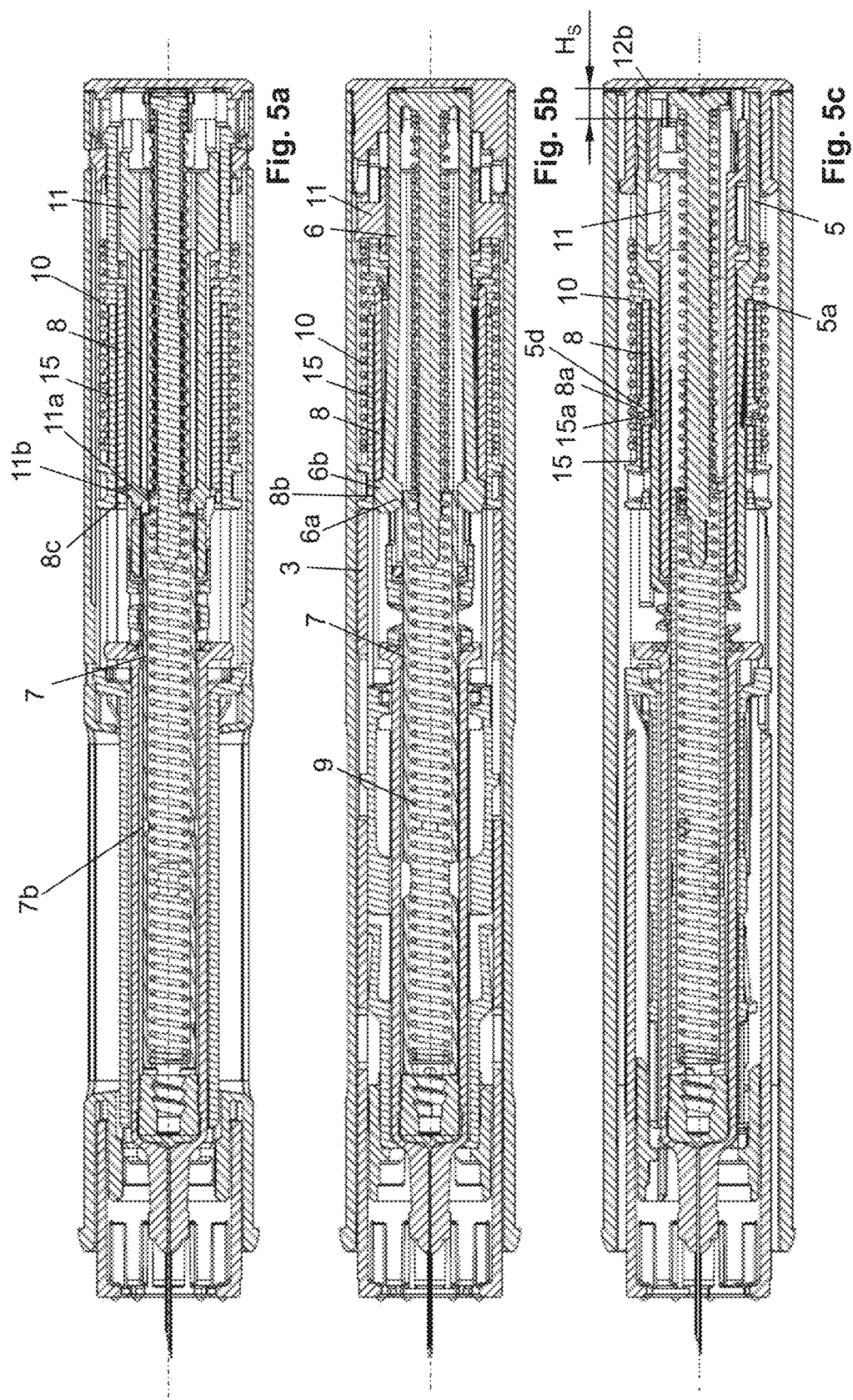

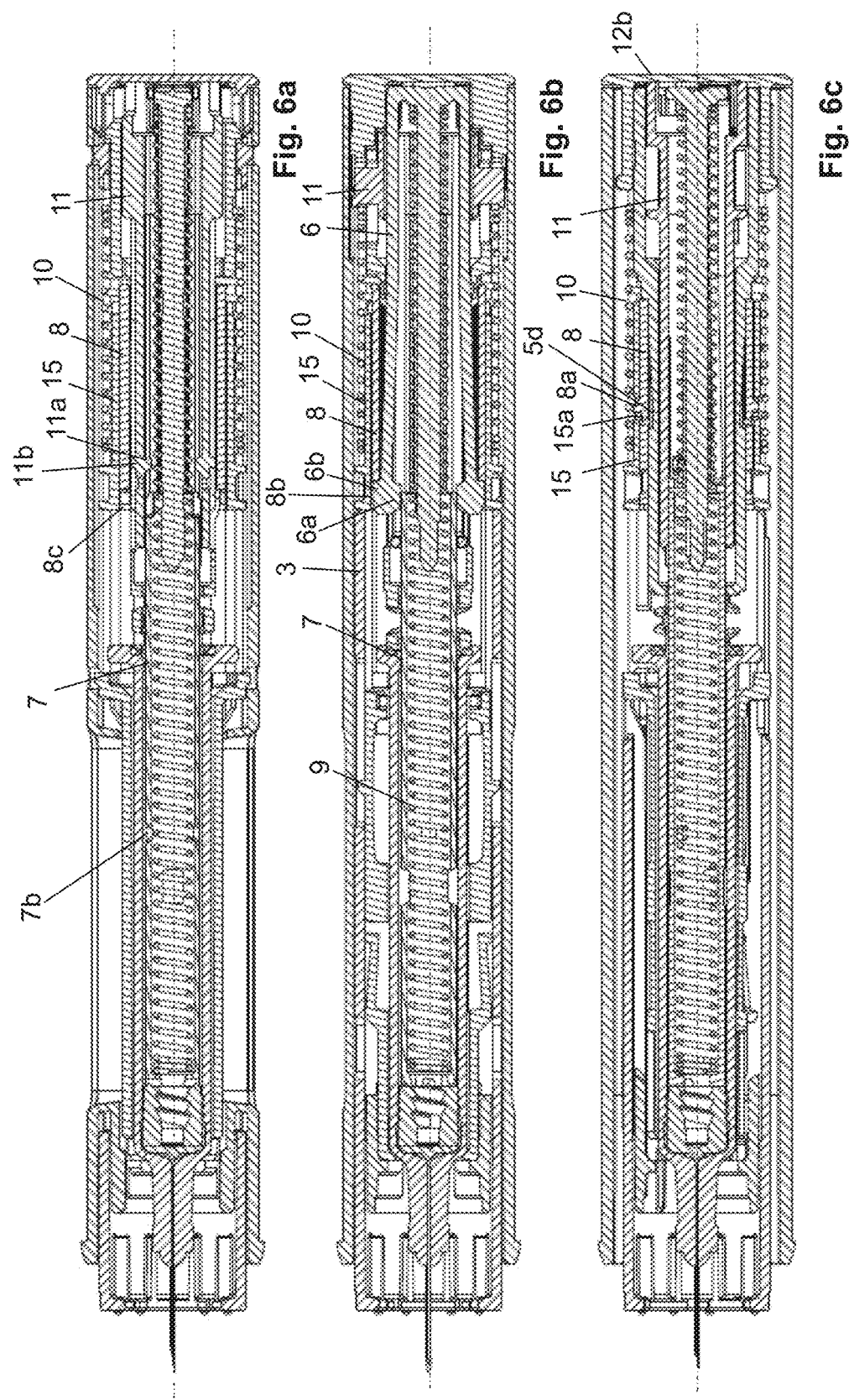

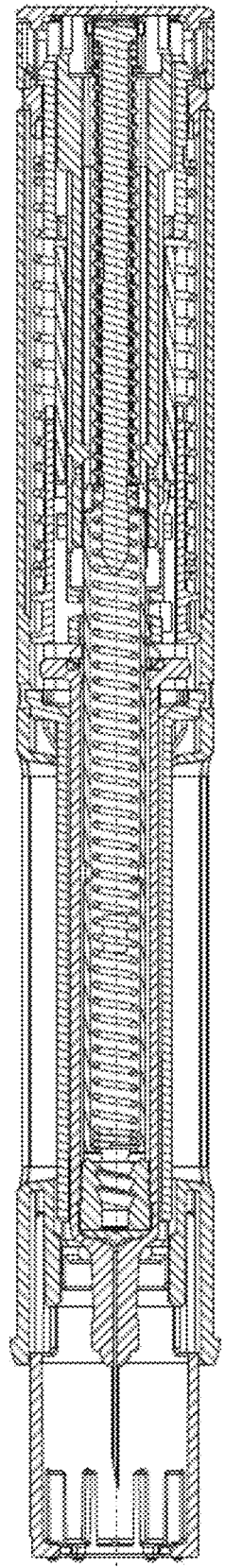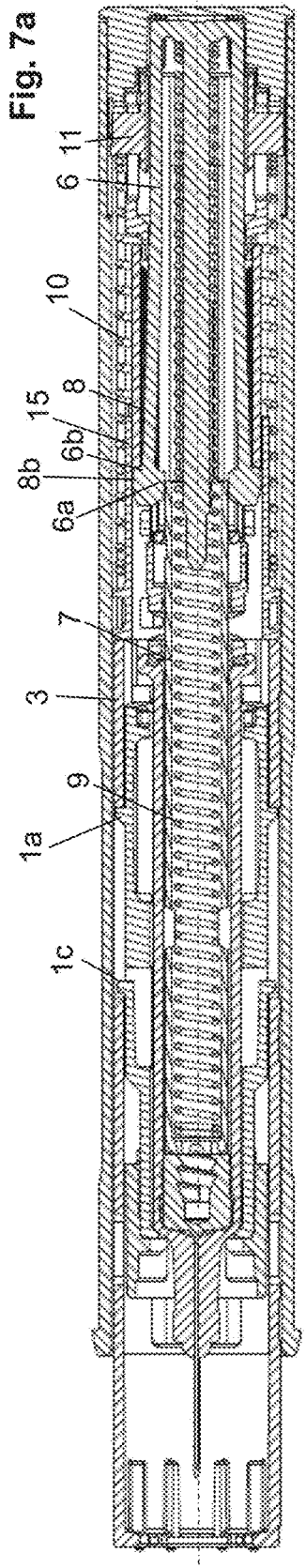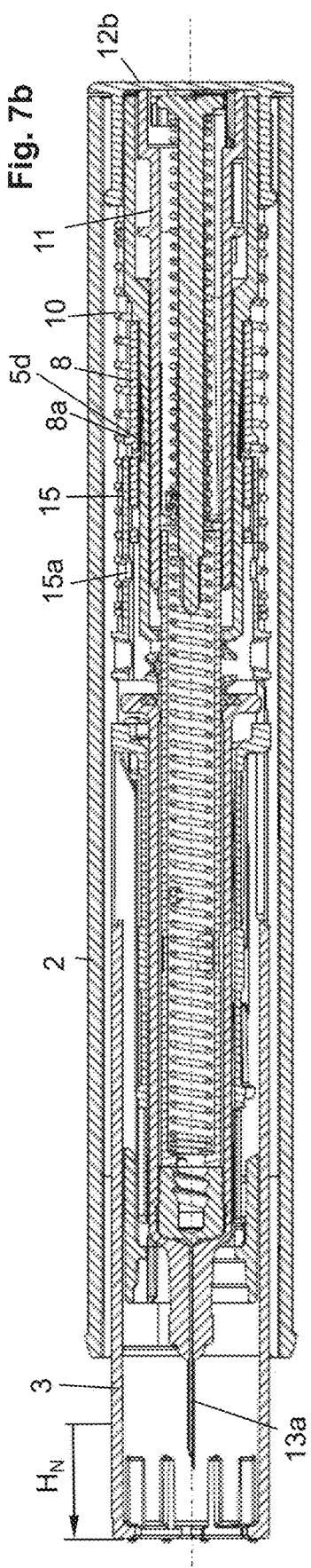

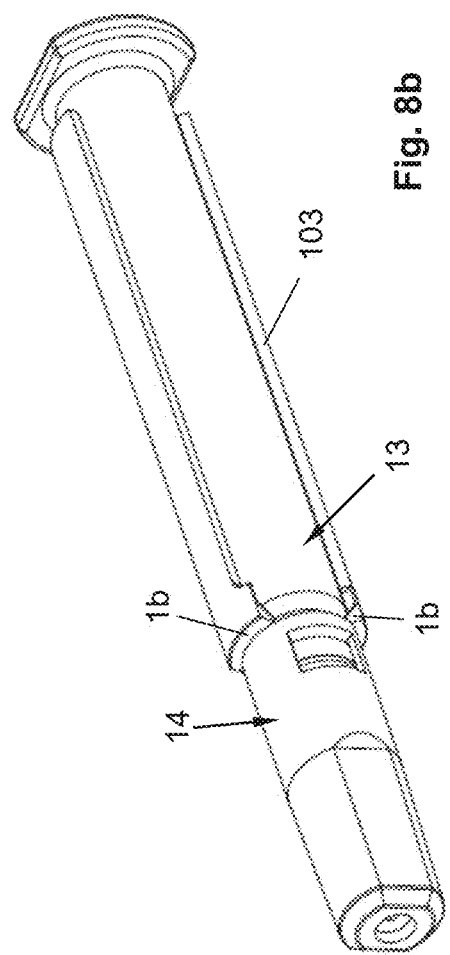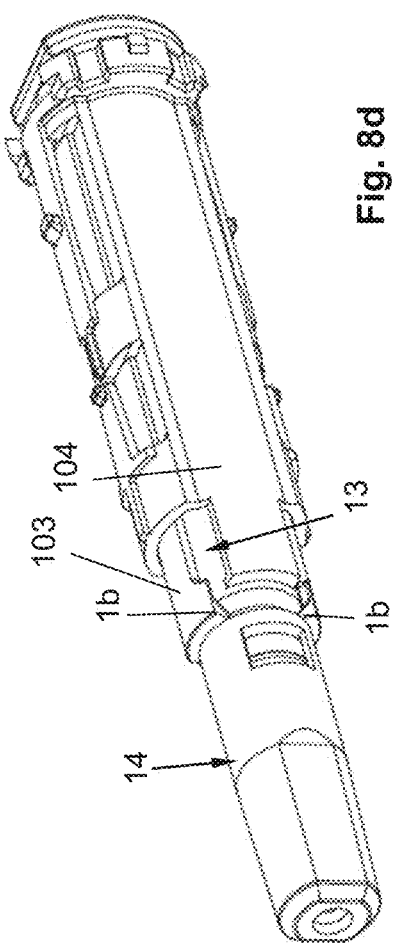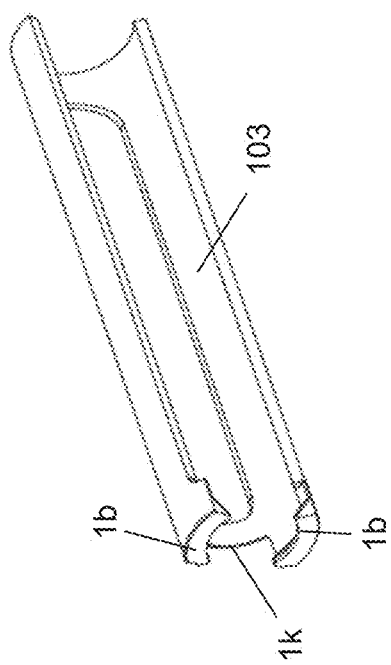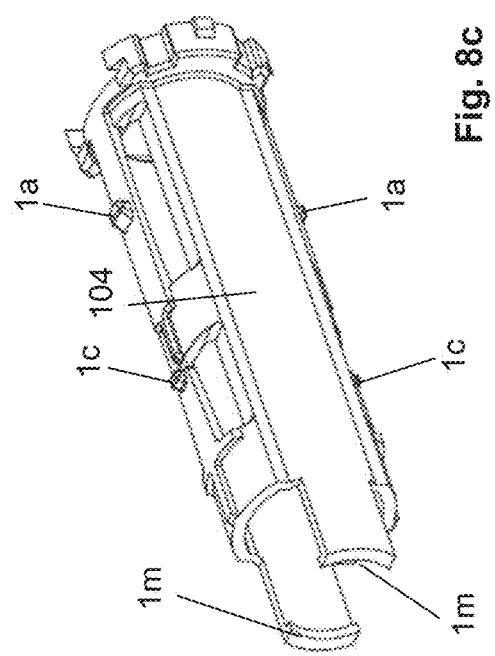

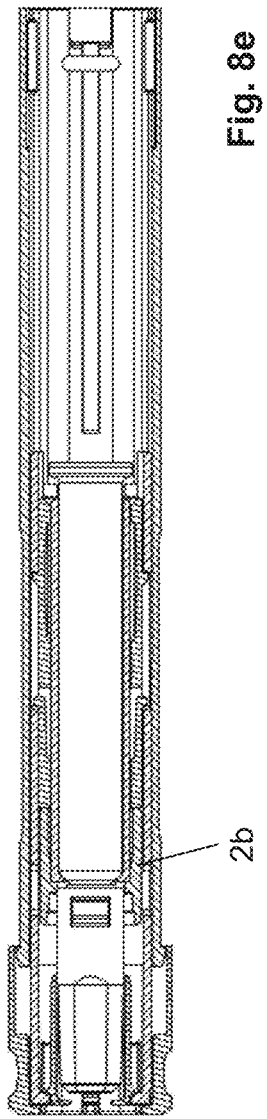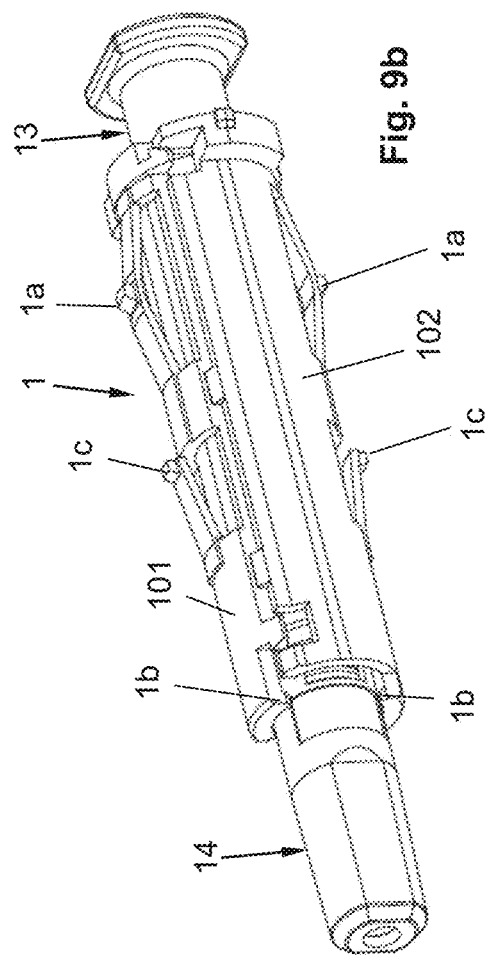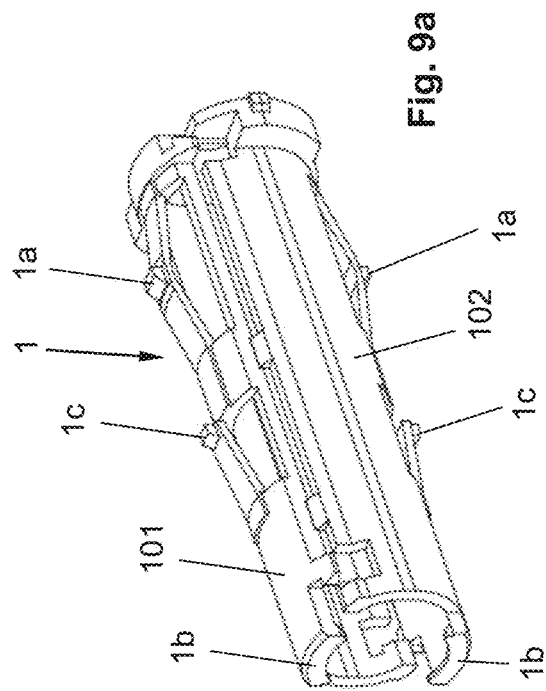

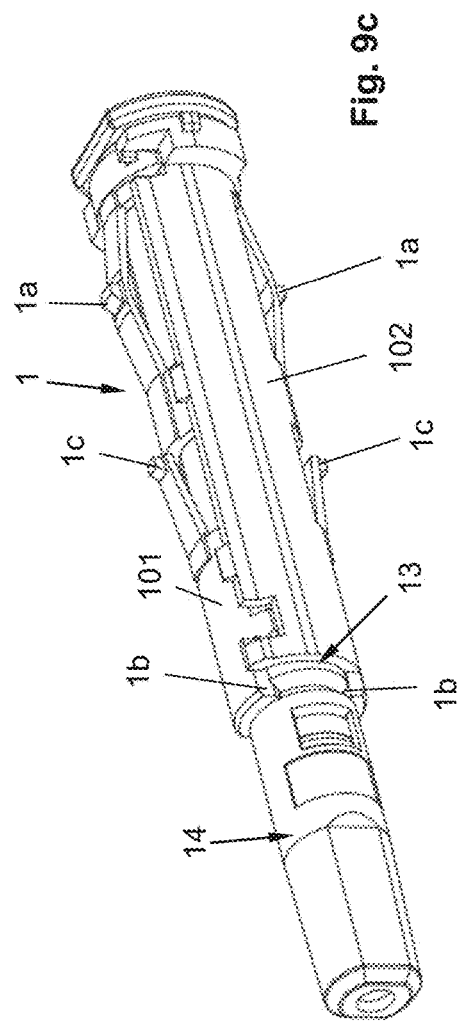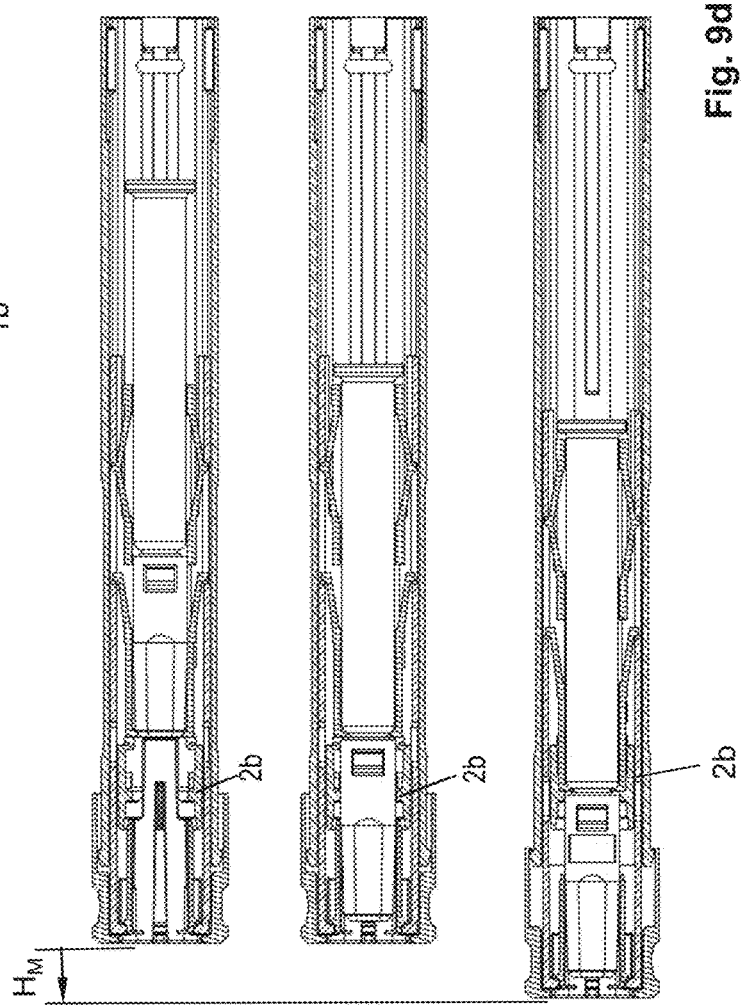

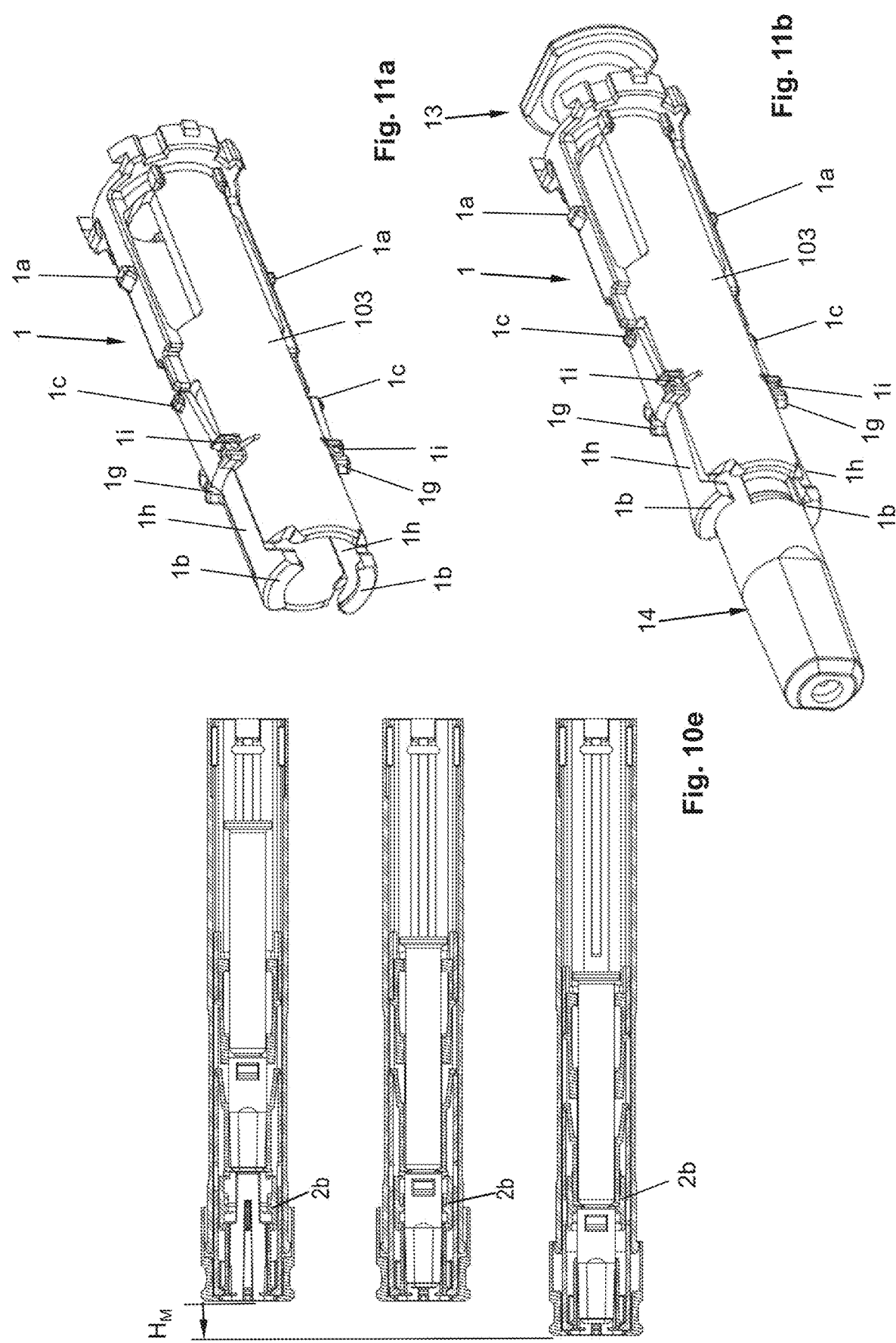

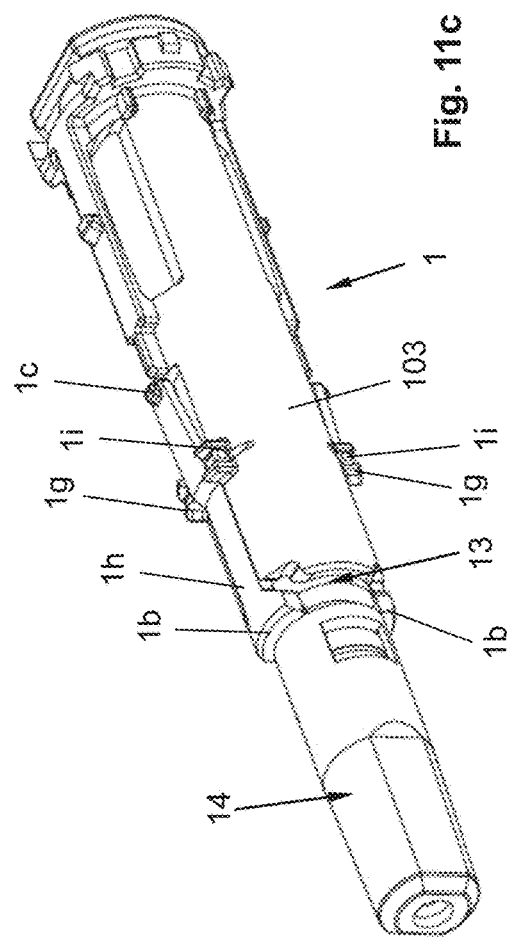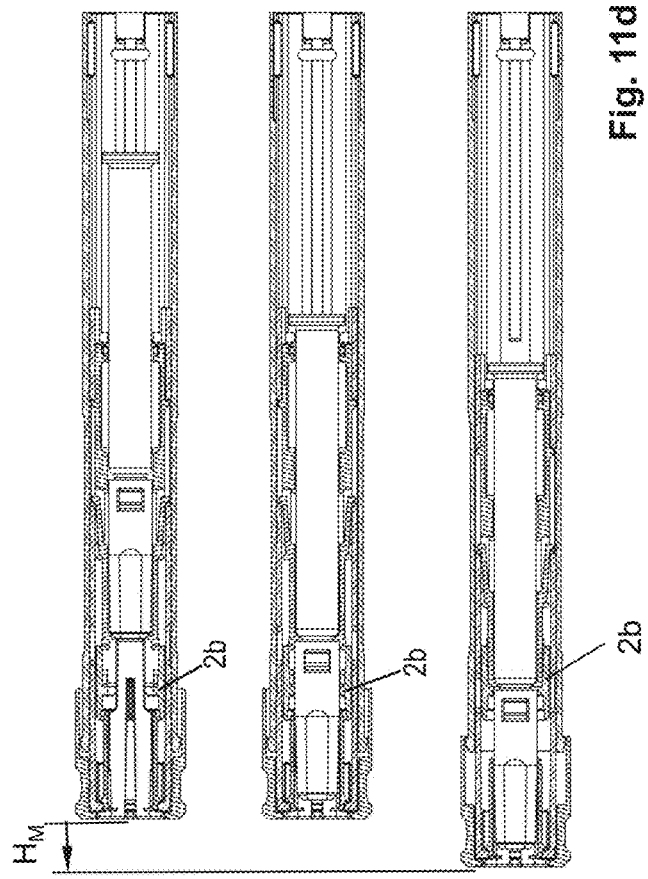

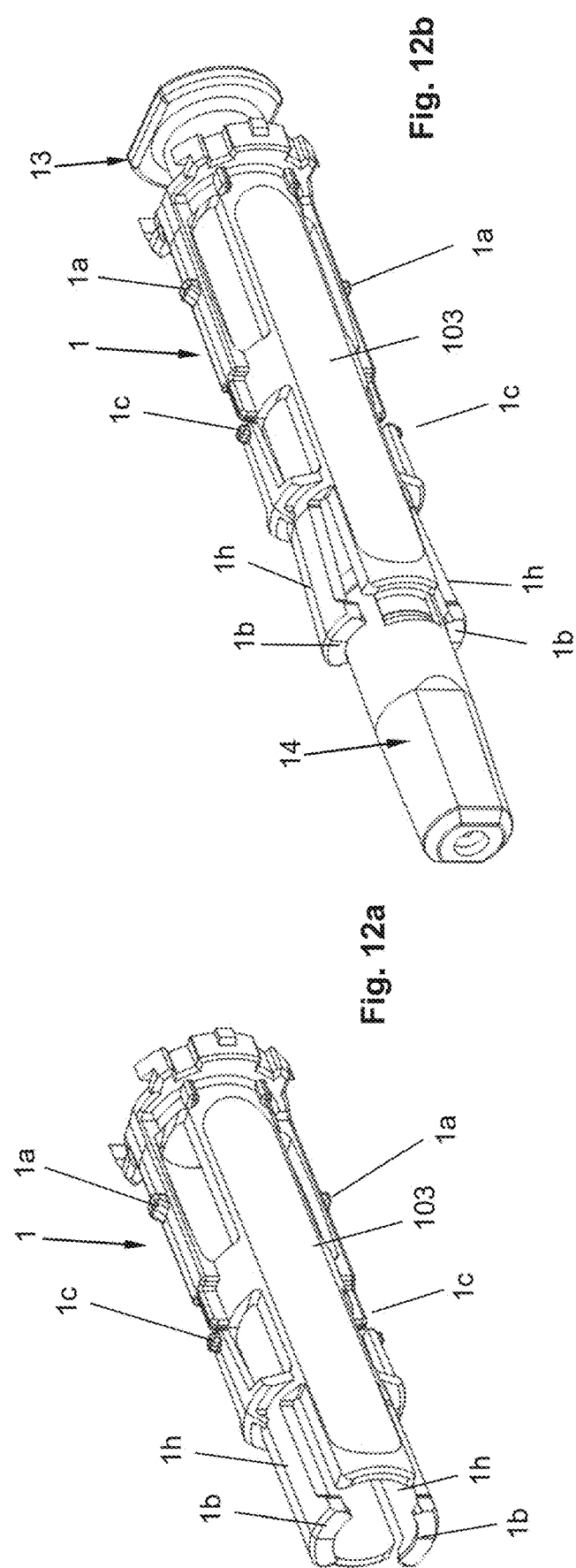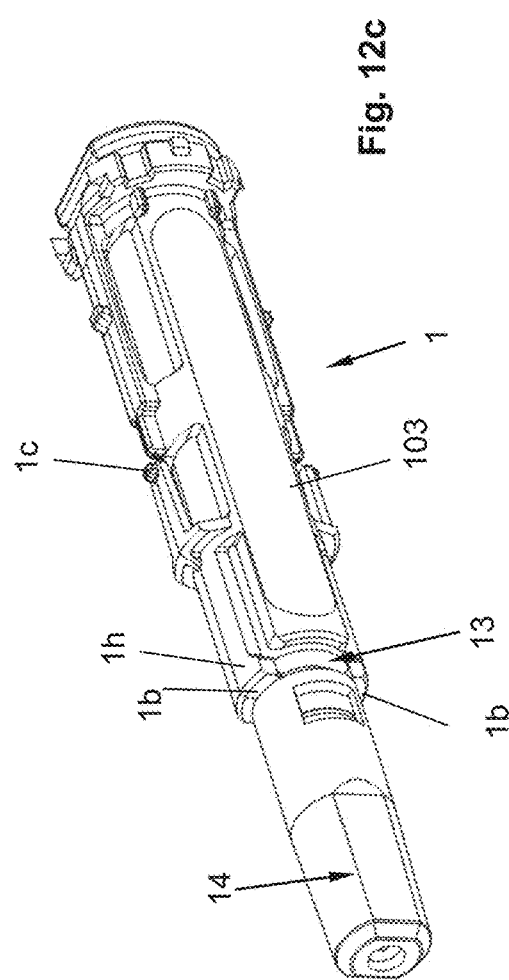

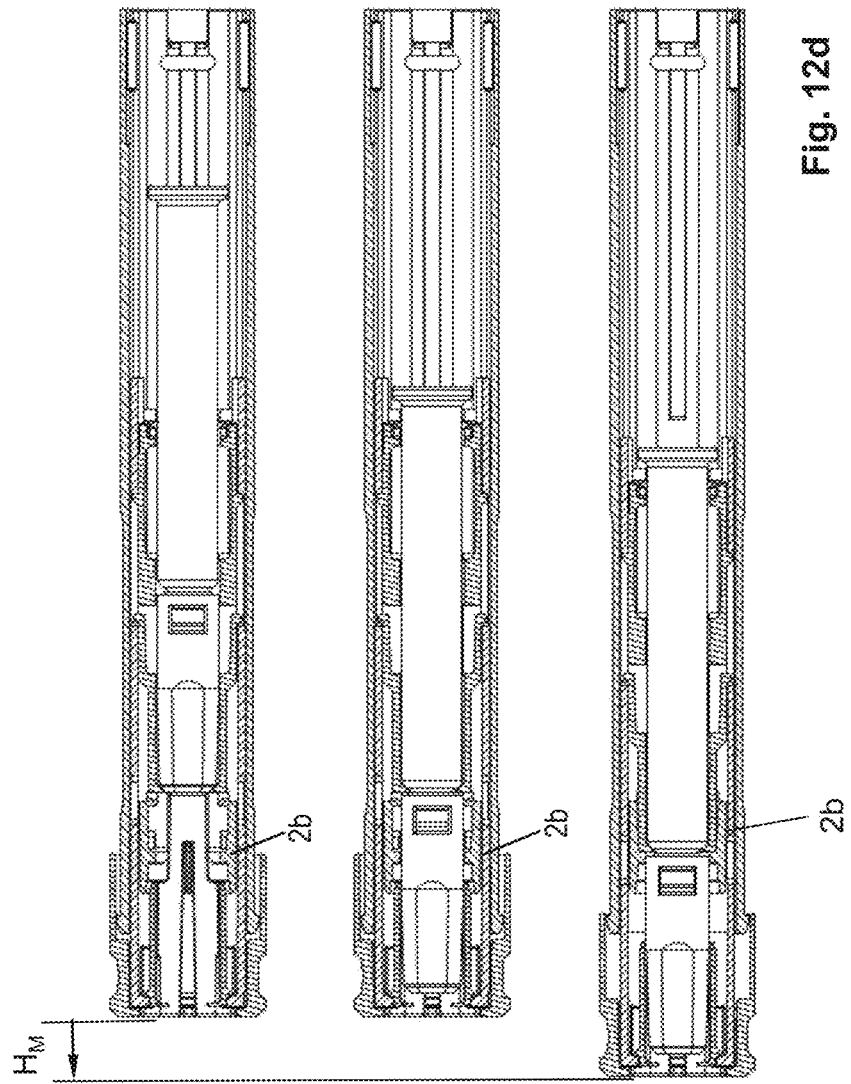

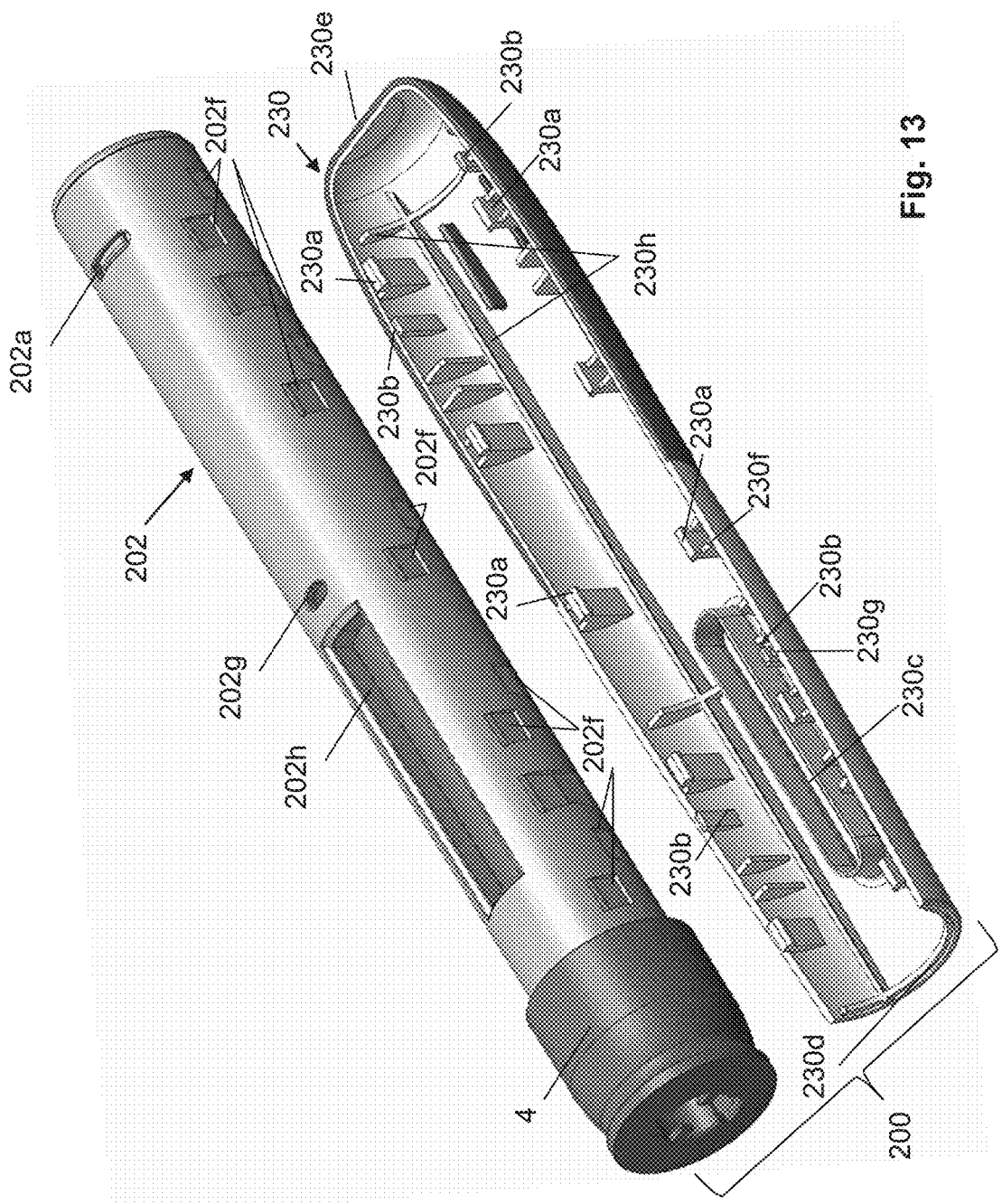

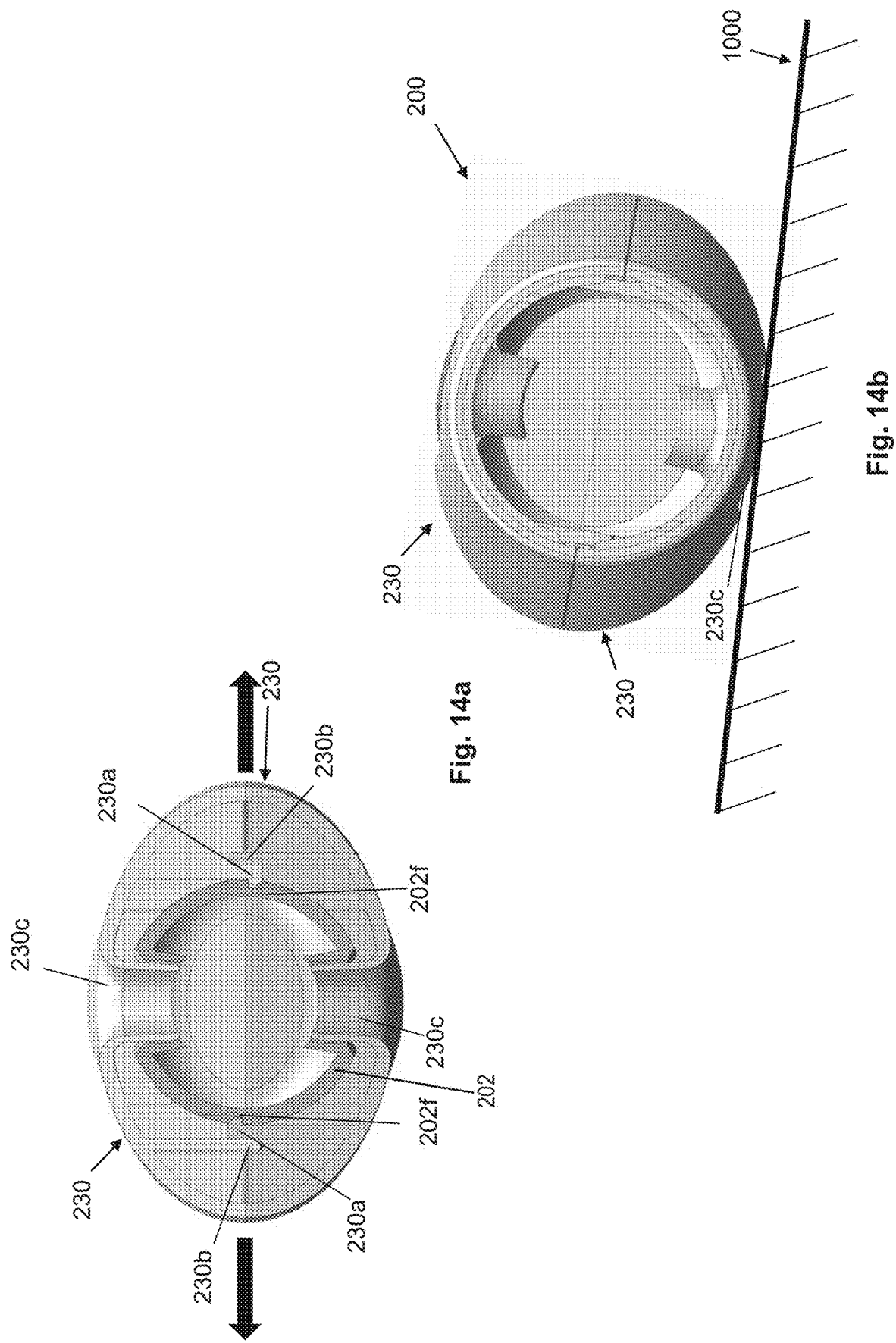

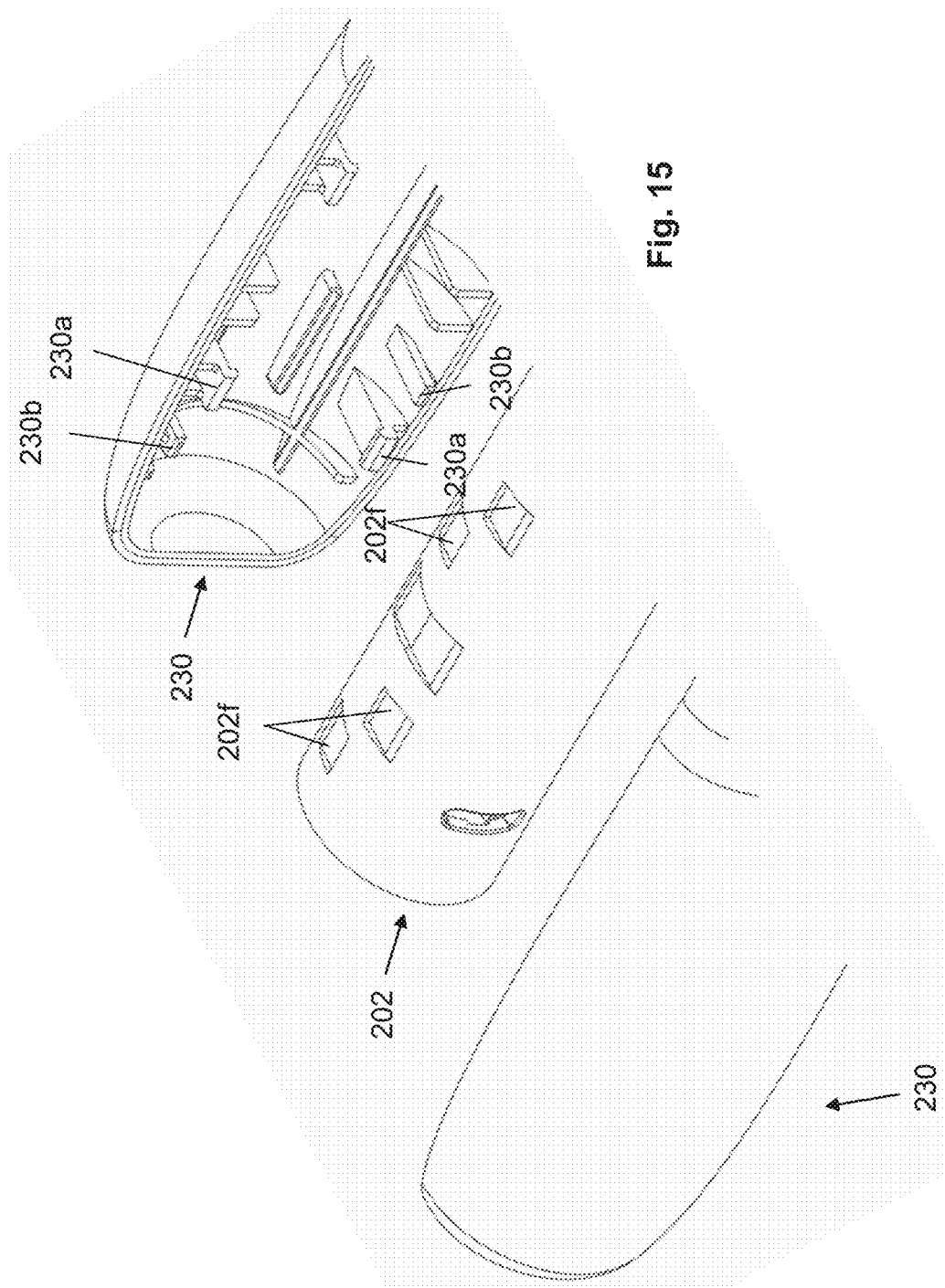

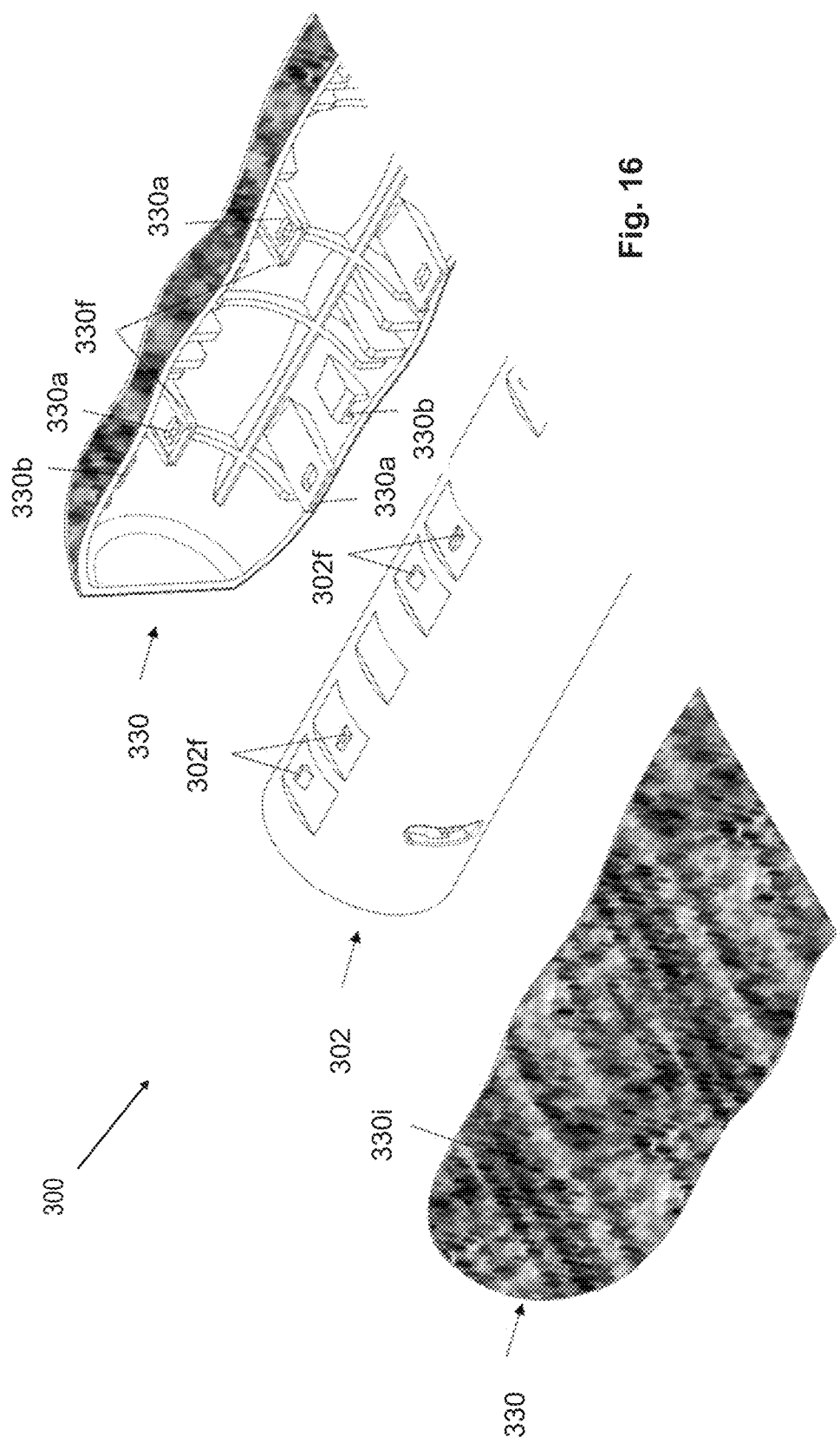

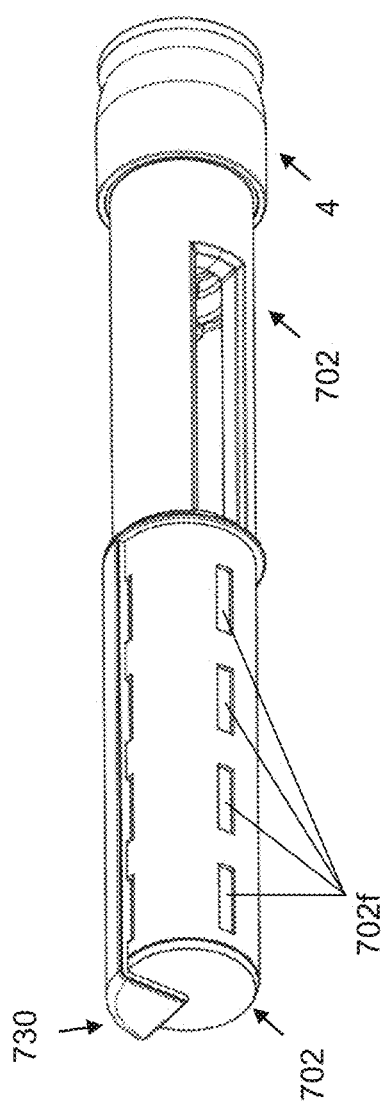
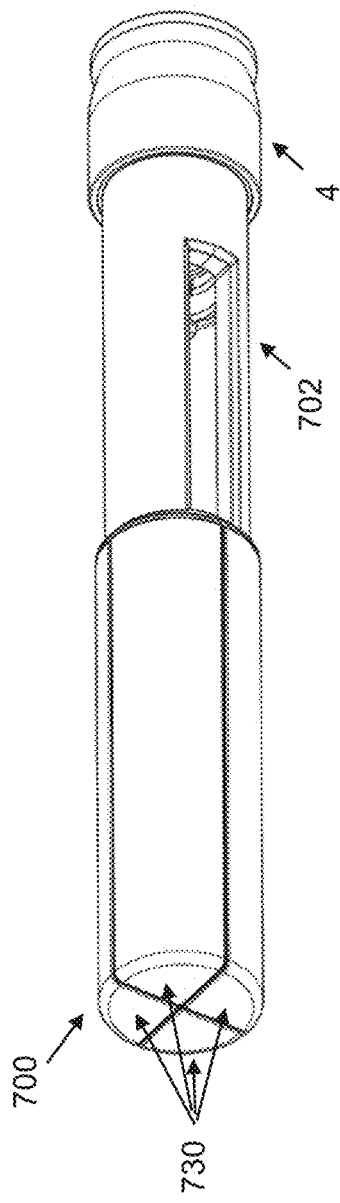
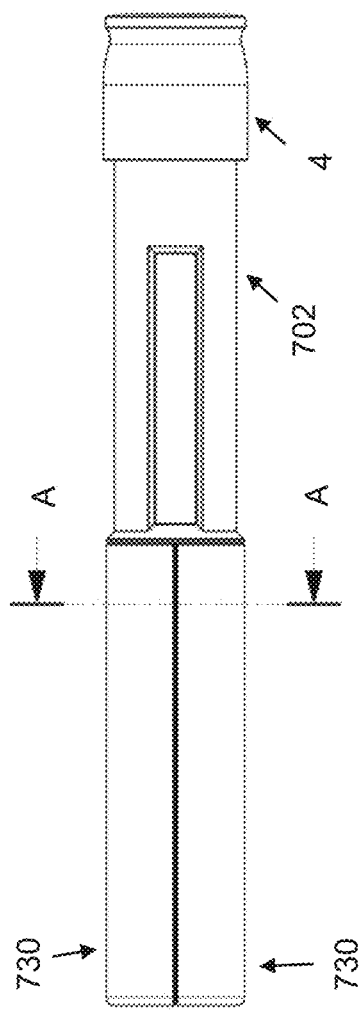

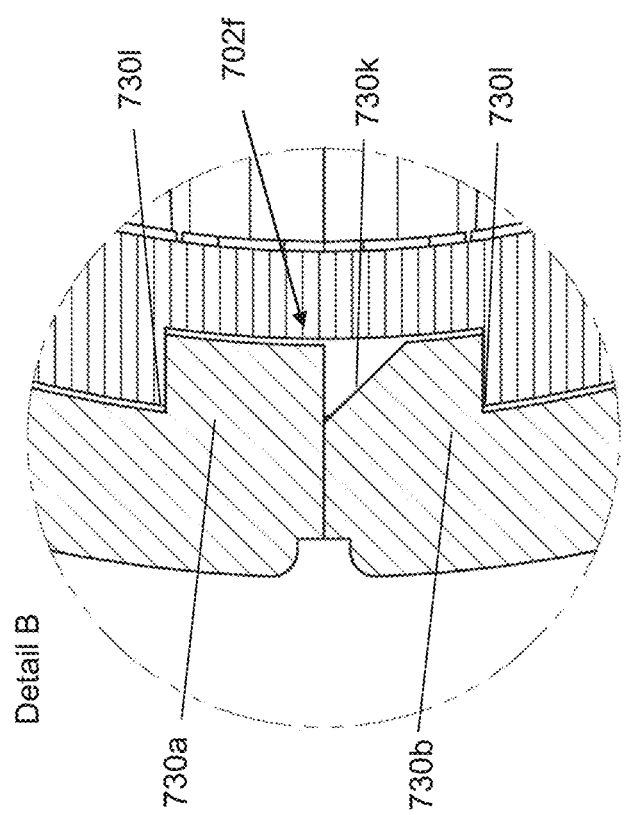
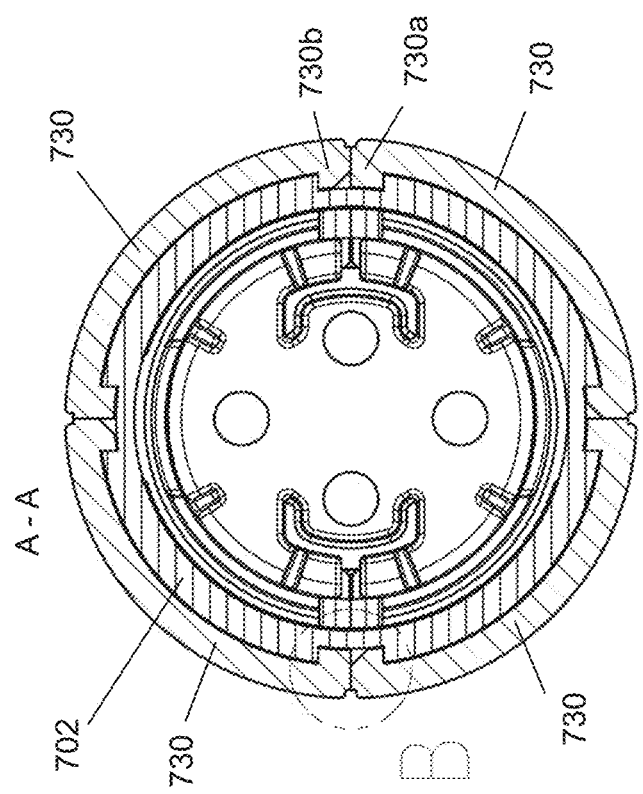
Fig. 21b
Fig. 21a

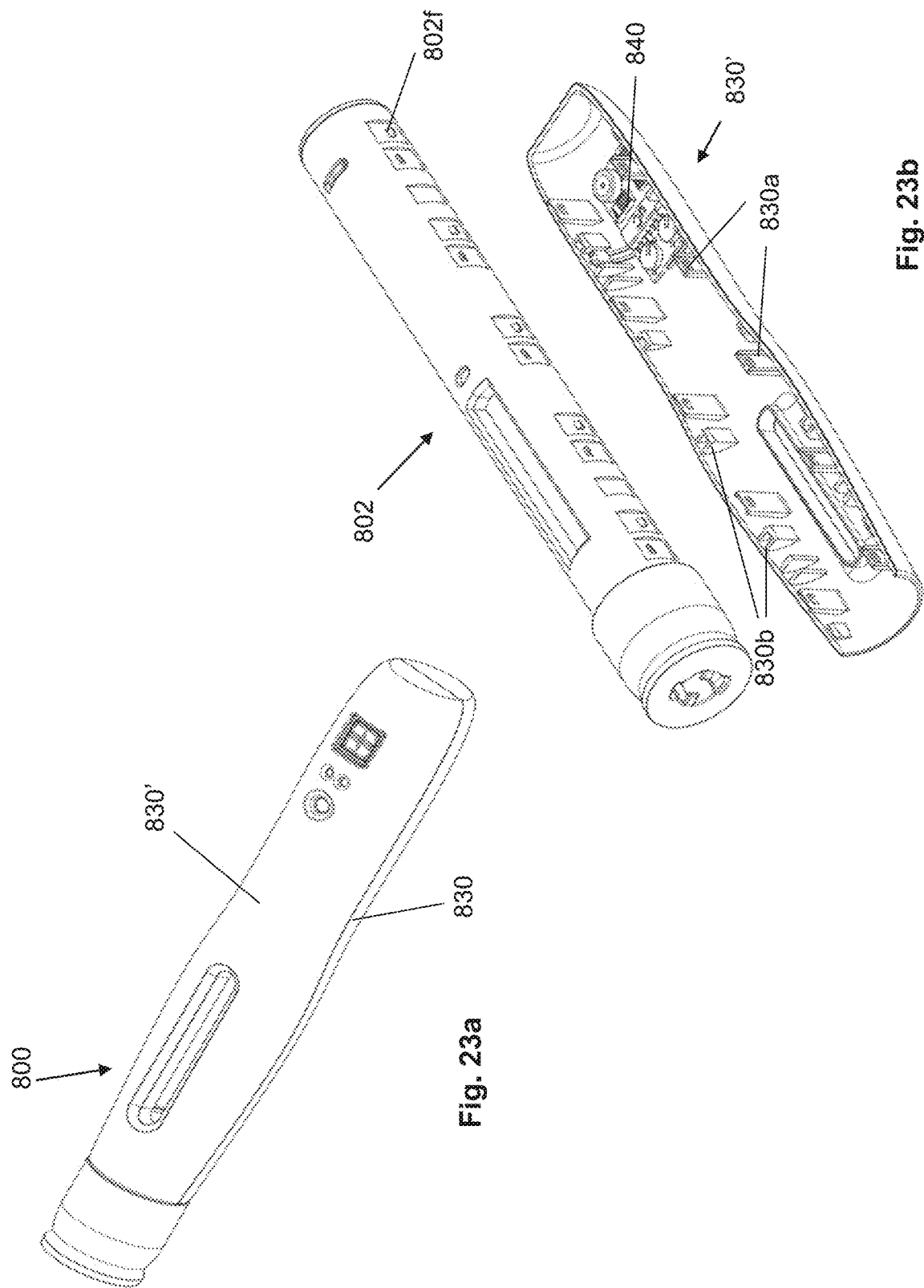

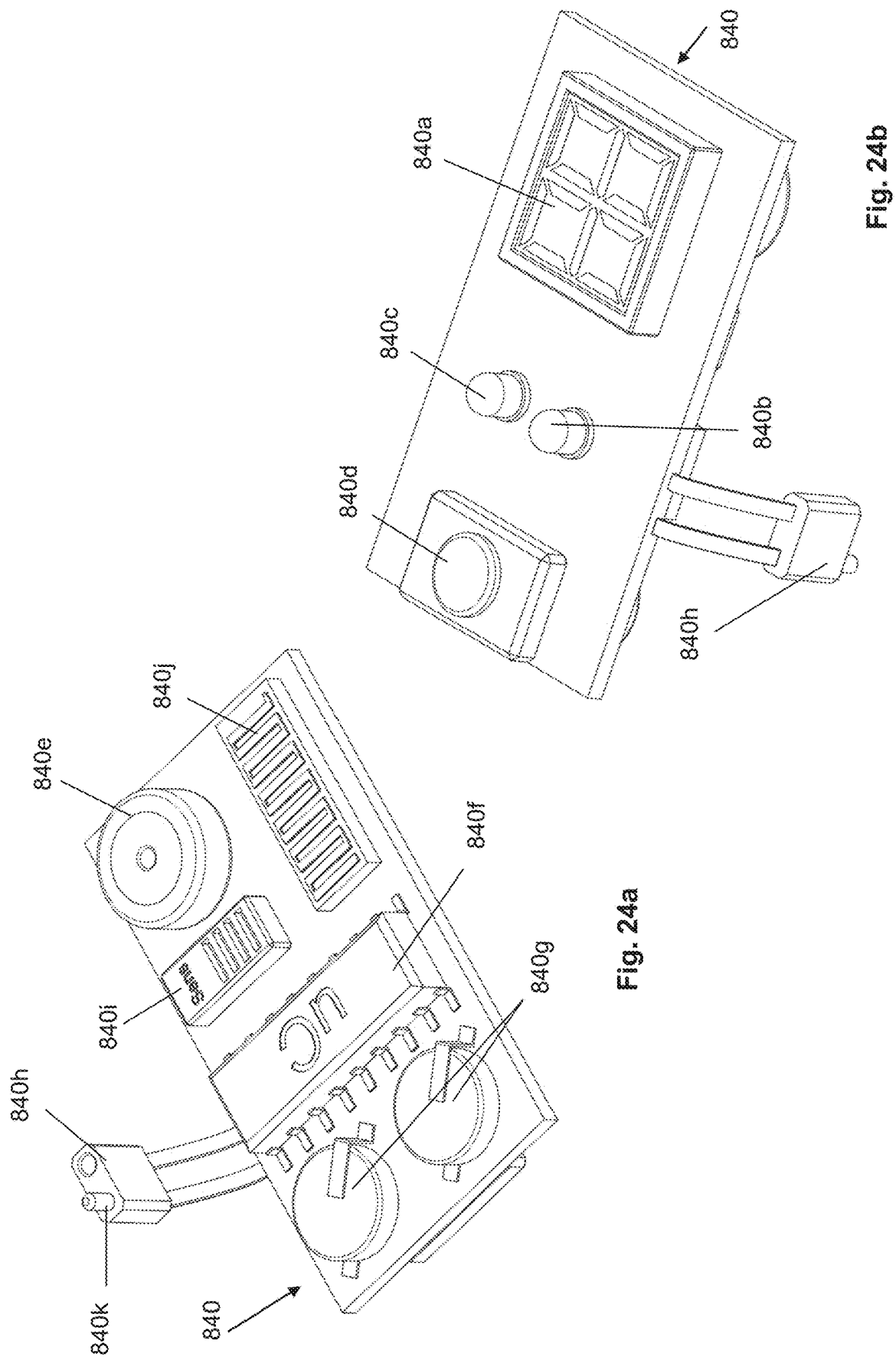

ADJUSTABLE INJECTION DEVICE

CROSS-REFERENCE TO RELATED APPLICATIONS

This application is a continuation of U.S. patent application Ser. No. 15/810,807 filed Nov. 13, 2017, issued as U.S. Pat. No. 10,610,646 on Apr. 7, 2020 which in turn is a continuation of International Application No. PCT/CH2016/000074 filed May 3, 2016, which claims priority to Swiss Application No. 667/15 filed May 13, 2015, the contents of all of which are herein incorporated by reference.

TECHNICAL FIELD

The invention relates to injection devices, particularly to injection pens and autoinjectors, by means of which a fluid product contained in a product container can be discharged. In particular, the fluid product is a drug. In particular, the invention relates to an injection device that can be adjusted cost-effectively to the requirements of different medical indications.

BACKGROUND

An injection device, such as an injection pen, an autopen or an autoinjector, can in principle be suitable for the administration of different drugs, provided the drug has a consistency that allows discharging with the injection device. However, differences result indirectly from the medical indications for which the different drugs are used. Thus, depending on the indication, different requirements are applicable in terms of size, shape, surface and mechanical properties of the housing of the injection device. Thus, in diseases such as multiple sclerosis (MS), for example, the patient's mobility can be impaired, so an injection device that is used for treating patients with MS is associated with special requirements in terms of the shape of the device, to allow the patients to be able to handle the injection device at all. Thus, in the case of medical indications that relate to the handling of injection devices by children or persons of small stature, it can be necessary to design the injection devices to be as slender and small as possible.

Here, the term "drug" comprises any flowable medical formulation that is suitable for the controlled administration through a means such as, for example, a cannula or hollow needle, comprising, for example, a liquid, a solution, a gel or a fine suspension containing one or more medical active substances. "Drug" can refer to a composition with a single active substance or to a premixed or co-formulated composition with a plurality of active substances from a single container. The term drug comprises medicines such as peptides (for example, insulins, insulin-containing drugs, GLP-1-containing preparations as well as derived or analogous preparations), proteins and hormones, biologically prepared or active substances, active substances based on hormones or genes, nutrition formulations, enzymes and other substances either in solid (suspended) or liquid form, but also as polysaccharides, vaccines, DNA or RNA, or as oligonucleotides, antibodies or parts of antibodies as well as suitable base substances, adjuvants and carrier substances.

An injection device is known from U.S. Pat. No. 8,535,274, in which a U-shaped shell can be snapped on in the area of the handle. This shell can be used for ergonomic as well as for decorative purposes and it can be replaced easily by the user. The U shape of the shell implies that the injection device cannot be enclosed completely by the sleeve, which limits the three-dimensional shaping.

A syringe with an additional housing sleeve is known from US2009/0157012, which is mounted in a slidable manner on the syringe. The sleeve, which can be manually shifted in the axial direction by the user, ensures visibility of the needle for protection before and after an injection. The sleeve can be detachably locked in several positions on the syringe. The sleeve can also be pulled off the syringe by the user.

An injection device is known from WO03/105927, in which a portion of the housing external surface can be provided with a surface-finish coating. This coating can be of purely decorative nature or it can have a function. In this invention, it is disadvantageous that the three-dimensional shape of the injection device can only be influenced to a minute extent.

An injection device is known from WO2011/124633, which can be supplemented on its lateral area with differentiation shells 204 and 206. These shells can be assembled by the trained user on the injection device and also removed again. Here, the differentiation shells 204 and 206 comprise snap connection elements designed to be complementary to one another, that is to say the differentiation shells 204 and 206 are not attached to the housing itself, instead the shells secure one another. Furthermore, the injection device is designed in such a manner that it can only be used if the differentiation shells 204 and 206 are mounted. The differentiation shells 204 and 206 thus influence the functionality of the injection device.

For manufacturers of injection devices, drug manufacturers, health insurers and persons to be treated, there is a need to have injection devices available that are as advantageous as possible while being reliable and effective. Accordingly, it would be desirable to have an injection device that has an invariable, proven, reliable and predetermined technical design with an invariable housing, wherein, via additional add-on parts, which are firmly and non-detachably connected to the housing, the shape, the haptics, the surface topography and the ergonomics of the injection device can still be adjusted during the production of the device, thus taking into account the requirements of the medical indications in a simple and advantageous manner.

SUMMARY OF THE INVENTION

The aim of the invention is to provide an injection device that can be adjusted cost-effectively to the requirements of different medical indications.

The aim is achieved according to the invention by the independent Claim 1; advantageous developments result from the dependent claims, the description and the figures.

The injection device according to the invention comprises an elongated housing, in particular in the shape of an elongated cylinder, and a product container arranged in the housing. The product container is preferably a prefilled syringe or a carpule. The product container can be arranged in the housing in a slidable manner or in a stationary manner. Furthermore, the injection device comprises a discharging mechanism that can cause a discharge of the product via a manual force action by the user or by an energy storage arranged in or on the injection device, such as, for example, a spring, a battery, a pressurized gas container, a gas generator or an osmotic drive device. Moreover, in the event that the product container is a carpule, the injection device comprises an injection needle that can be attached in a detachable manner to the housing and that establishes a fluidic path between the carpule content and the injection tip. If the product container requires a prefilled syringe with firmly attached injection needle, no separate injection needle is necessary.

In an additional aspect, the injection device moreover comprises a dosing device that enables the setting of a predetermined portion or dose of the product present in the product container, wherein, with the discharging mechanism, the set dose is subsequently discharged. Here, the dosing device and the discharging mechanism can be designed in such a manner that either exactly one dose can be discharged or several doses can be discharged one after the other from the same product container. In an additional aspect, several doses of equal size can be discharged by means of a discharging mechanism. Alternatively, if the injection device is implemented as a conventional autoinjector, no device for dose setting is necessary, since only one preset dose can be administered.

In an additional aspect, the injection device can be intended for single use, so that the device has to be disposed of after the product container has been emptied. In other embodiments, the product container can be replaced, and the injection device can thus be designed to be reusable. Alternatively, parts of the injection device can be replaceable together with the product container, resulting in a so-called semi-disposable system.

In an additional aspect, the injection device can comprise a needle protection sleeve that covers the injection needle. In a preferred form, the needle protection sleeve can be moved for the injection of product in a direction such that it unlocks the injection needle for the injection. In an additional preferred form, after the injection, the needle protection sleeve moves back again over the injection needle and is firmly locked relative to the housing, so that additional puncture processes, particularly undesired puncture processes, are no longer possible.

In an additional aspect, the injection device can comprise a pull-off cap that covers the end of the injection device and accommodates the injection needle. The pull-off cap can protect the injection device before the planned use against unintended triggering or it can protect the needle protection sleeve against undesired manipulation, for example, during transport or during the unpacking process. In an additional aspect, before use, the pull-off cap can be used to remove any needle protection cap present from the injection device; for example, such a needle protection cap is conventionally used in prefilled syringes, particularly to keep the needle sterile.

The housing of the injection device is preferably elongated and forms the longitudinal axis of the injection device. The housing is preferably in the shape of a sleeve and/or cylindrical, in particular circular cylindrical. Fastening points according to the invention are arranged on the housing external side. Preferably, in each case two fastening points are diametrically opposite one another on the lateral area of the housing. In preferred embodiments, two to sixteen fastening points are arranged on the outer surface of the housing; however, this number can also be larger or smaller. In advantageous embodiments, the fastening points can extend in the axial direction and be designed in the form of fastening channels or strips instead of individual points.

In an additional aspect, the injection device according to the invention comprises at least two housing-like shells that can be attached to the external side of the housing, as explained in detail below. The housing-like shells in each case comprise at least one holding device that is geometrically arranged such that, when the shell is attached to the housing, they come to lie in a fastening point and thus at least contribute to the fastening of the shell on the housing. Preferably, the shells comprise a plurality of holding devices, in order to be able to achieve a reliable fastening of the shells to the housing. In preferred forms, the holding devices are snap arms or tabs, which, with the fastening points designed complementary thereto, snap on or in the housing, as a result of which the shells are held on the housing. In some design forms, the snap arms or the tabs are arranged relative to the lateral area of the housing so as to be tangential to the cross section, if the associated shell is fastened to the housing.

Moreover, in each case the shells comprise at least one blocking device. The function of a blocking device of a shell is to prevent, after the fastening of the shells to the housing, a disengagement of the holding devices of another shell from the housing. Preferably and in reference to the preceding paragraph, the at least one blocking device of a shell is designed in particular so that it can prevent a radial deflection of a snap arm or of a tab of another shell, so that said shell is fastened to the housing. Thus, the shells are connected in a non-detachable manner (in particular by positive connection) to the housing. Non-detachable means that the shells cannot be separated, in particular in a destruction-free manner or without a special tool, from the housing.

In a first preferred embodiment of simple design, the injection device comprises two housing-like shells that are identical so as to be interchangeable. Here, the shells are configured as semi-shells. In this simple embodiment, the two semi-shells complement each other to form a cylinder jacket, which is preferably circular cylindrical, if they are attached to the housing. In cross section, the semi-shells are approximately semicircular, wherein the two half-shells in cross section can complement each other to form a closed circumference, preferably a circle. Along the open shell edges of the lateral area, the holding devices, in particular in the form of snap arms, or the blocking devices, in particular in the form of ribs, are arranged on the inner surface of the shells, wherein they definitely can protrude approximately in a tangential direction over the open end of the respective shells. In the present embodiment with two identical semi-shells, on a shell, a blocking device and a holding device lie opposite one another at axially the same height at the open shell edges, that is to say diametrically opposite one another. In this arrangement, if one uses two identical shells and one assembles them to form a cylinder, then the holding device and the blocking device during the assembly come to lie exactly on top of one another, wherein the blocking device has to lie farther outward in the radial direction in order to prevent an outward deflection of the holding device. It can be appropriate to have a plurality of holding devices and also a plurality of blocking devices on a shell in order to optimize a secure and firm seat of the shells on the housing. Here, it is not necessary that a blocking device is associated with each holding device. For the design according to the invention, that is to say for the non-detachable connection between shells and housing, only at least one holding device for each shell has to be blocked by a blocking device of another shell.

Advantageously, in this simple embodiment, the semi-shells are identical and, therefore, the production of the semi-shell shells is more advantageous. For example, if the semi-shell shells are produced from plastic in the injection molding process, then only one tool is necessary for the two semi-shells, which considerably reduces the production costs.

From the above description, it is immediately clear to the person skilled in the art that, in the case of an invariable housing of the injection device, the shells can be designed very freely, as long as the position of the fastening points on the housing are taken into consideration, and the holding devices and the blocking devices on the shells are arranged so that they fit with the fastening points or the holding devices. Here, it is not necessary that a holding device is associated with each fastening point present on the housing. Theoretically, one holding device and one blocking device would be sufficient for each shell in order to connect the two shells in a non-detachable manner to the housing. However, it is preferable to use more fastenings, in order to optimize a reliable seat of the shells on the housing. Moreover, it is not necessary to make each fastening non-detachable by a blocking device; it is sufficient if in each case, for each shell, one holding device is blocked by a blocking device of another shell.

In the case of outwardly expanding shell geometries, this means that, if the radius of a shell in the axial position of the fastening point on the housing is greater than the housing radius, then holding devices or blocking devices are simply radially offset inward in the interior of the shell, so that holding devices or blocking devices fit with the fastening points of the housing. In this manner, the shape of the injection device can be adjusted to the requirements of the medical indication, without having to change the injection device itself.

In additional designs, the injection device comprises two housing-like shells which can differ in shape, material, color and/or haptics. Analogously to the design of the first embodiment, on the semi-shells of the additional designs, holding devices and blocking devices are also arranged so that the shells can be attached in a non-detachable manner to the housing of the injection device. The fact that the shells differ in these designs opens additional possibilities in the adjustment of the injection device to the requirements of the medical indication. Thus, asymmetric handles, in particular ergonomic handles, can be implemented, without changing anything on the injection device itself.

In one design, an opening is present on the housing of the injection device, which makes it possible, for example, to see the product container, so that an opening, such as a window (with or without windowpane), for example, can also be provided on one of the shells, which can be greater than or of the same size as, or smaller than the opening in the housing, and which, if attached to the housing, opens an at least partial view through the opening of the shell and of the opening of the housing onto the product container. Naturally, such openings are also conceivable in the first above-described embodiment, wherein the housing then preferably comprises two housing openings that face one another. If the opening of the shell is smaller than the opening of the housing, then, for example, the product container can be partially filled, without the user being able to see this, since the opening in the shell is then advantageously adjusted to the filling level. Here, a modification of the housing is then unnecessary. Advantageously, the opening in the shell has a radially inward directed collar, which obstructs the view onto housing portions present and mechanically stabilizes the shell.

In one design, openings in the housing-like shells enable access to functional features of the injection device such as buttons, particularly trigger buttons and/or dose setting buttons, locking devices, displays, sensors, emitters, receivers, needle protection sleeve locking devices, dose displays, priming displays, end-of-content displays, light-emitting elements, acoustic signal generators, skin sensors, emitters of electromagnetic radiation, light sensors, and others. In order to allow the operator to access the functional elements of the injection device, the individual housing-like shells can have a multipart structure, in particular, they can be provided with movable parts such as pushbuttons or buttons that transfer the actuation by the operator to the functional features on the housing of the injection device and as a result bring about an actuation of these functional features on the housing. Multipart can also mean that, in certain areas of the housing-like shells, areas having increased transparency are present, that is to say inspection windows that open the view onto certain housing areas. These windows can be designed as optical magnifier.

In the housing of the injection device, openings can be present, through which elements can be introduced into the housing interior and which can interact with elements of the injection device contained therein. The above-described buttons are examples of such elements that can engage in the housing interior. However, it is also conceivable and advantageous to use pushbuttons, contacts, switches, electrical or optical conductors.

In certain designs, the fastening points of injection devices according to the invention can comprise areas on the housing that are optically or electrically conductive. The purpose of this is to be able to introduce light or electrical current into the housing interior or to lead light or electrical current out of the housing interior. Here, light and electrical current should be understood to mean that, for example, energy as well as information transfer can be included. In these designs, it is advantageous if the holding devices (and/or the blocking devices if applicable) that are attached to the conducting fastening points also have optically or electrically conductive areas, so that transmission of light or electrical current or radiation in general is enabled between housing-like shells and the housing interior. In this manner, sensors arranged in the housing interiors and actuators can be controlled, queried or scanned by control units, in particular, electronic control units that are arranged outside of the housing.

Depending on the geometry of the housing like shells, particularly in the case of outwardly expanding geometries, the space between the housing and the shell forms hollow spaces, which can be used advantageously so that additional interesting designs of an injection device according to the invention are formed. Thus, the hollow spaces, for example, electronic assemblies, can be arranged on the inner side of at least one portion of the housing-like shells. These electronic assemblies can be used for controlling, monitoring, communication or for status signaling of the injection device according to the invention. Moreover, the housing-like shells of these designs can have electronic display elements such as displays or simple light elements. Moreover, on housing-like shells of this design, antenna elements can be arranged, which enable wireless information transfer. To supply the electronic assemblies and other components with power, an energy storage in the form of a battery, an accumulator or a capacitor can be provided on the shells. If a plurality of assemblies is arranged on the shells, they can be connected and/or linked to one another and form circuits.

For communication, the housing-like shells can contain RFID or NFC circuits. The shells can also comprise WLAN or Bluetooth modules. By means of these communication means, the injection device can wirelessly transmit information to other devices, such as measuring devices, remote controls, management devices, smartphones, computers or computer networks. Conversely, the injection device can receive information and instruction from external devices.

In one design example, a housing-like shell comprises an electronic circuit for the unlocking of the injection device. For this purpose, the circuit comprises communication means in the form of a Bluetooth module as well as an electromechanical actuator, which can pull a cotter pin, which is movably arranged on the shell, into the housing or out of the housing, through an opening in the housing. The cotter pin, if inserted in the housing, prevents a triggering of the injection device, in which it blocks the discharging mechanism relative to the housing. If the cotter pin is pulled out of the housing by the electromechanical actuator, then the discharging mechanism is unlocked and can be used by the user for discharging a drug. Now, in this embodiment, it is interesting then that the command to pull out the cotter pin can be sent via Bluetooth to the injection device. Thus, the command can be transmitted via Internet to a smartphone of the user. Subsequently, a smartphone app forwards this command via Bluetooth to the injection device. Consequently, this means that, for example, a treating physician or an insurer can authorize the administration of a drug via Internet. This design can be supplemented moreover in that the electronic circuit also comprises a sensor that can detect the triggering of the discharging mechanism of the injection device. Advantageously, the sensor is implemented as a microphone that can recognize the characteristic acoustic pattern of the discharging mechanism. The microphone has the advantage that it does not have to be led through an additional housing opening into the housing, but can instead be arranged simply in a hollow space between the housing and the housing-like shell on the inner side of the shell. As soon as the microphone has recognized the corresponding acoustic pattern of the discharging mechanism, the circuit generates corresponding information that can be sent via Bluetooth to the smartphone of the user and from there via Internet to the treating physician, the insurer or a protocol server. If a plurality of doses of the drug can be discharged with the injection device, then the microphone can recognize a plurality of acoustic patterns. Assuming there is a corresponding electronic circuit, the acoustic pattern can also be used to determine the size of a dose. This enlarged design thus enables compliance verification by the physician or insurer. The fact that the electronics of the injection device are located exclusively in one of the housing-like shells makes it possible to cost-effectively produce different versions of the injection device. Thus, on the same housing, housing-like shells with or without additional function can be attached. In a variant of the present example, the actuator with the cotter pin could be omitted. As a result, the discharging mechanism would no longer be blocked, but, conversely, it would also no longer have to be unlocked via a smartphone. The part of the injection device that is arranged within the housing is not changed by the modification. And since the housing-like shells cover the housing opening that is provided for the introduction of the cotter pin, the user also does not notice that potential additional functions would be present.

In one design, one of the housing-like shells comprises an electronic circuit for training the user and for a subsequent unlocking of the injection device. The unlocking can occur, as described above, via an electromechanical actuator and a cotter pin. In this design, the circuit also comprises a voice output loudspeaker, wherein the loudspeaker is integrated in the housing-like shell. The circuit moreover comprises a nonvolatile storage for storing voice instructions, for example, in the form of an MP3 or AAC file, which can be converted by the circuit into an analog signal and output as voice announcement via the loudspeaker. Moreover, the circuit is connected to an operating element arranged on the housing-like shell, for example, a button on the external side of the shell. In order to unlock the injection device, the user must actuate the operating element, as a result of which the output of the voice file by the circuit is initiated. The user can now listen to the voice file, which can contain user instructions. After the voice output has ended, the circuit can pull the cotter pin via the actuator out of the housing and thus unlock the injection device for use. In an enhancement of the design, after unlocking, during and/or after the use of the injection device, additional voice files can be output automatically or after actuation of the operating element. In this way, the complete operating instructions can be stored in a housing-like shell and output automatically to the user depending on the operating steps. In injection devices that can be used for a plurality of doses, the speech files can be output for each use or only for the first use. Here it is also conceivable that the cotter pin, after each use, is retracted back into the housing and blocks the discharging mechanism again after the completion of each use. If the injection device can be used only once and the user requires daily injections, for example, sets of a plurality of injection devices in a package are typically dispensed to the user. Here, the versatile design of the injection device makes it possible that, without high added costs, for example, one injection device can be provided with the voice output, and the other injection devices of the set are not provided with voice output. This variant can be implemented in the simplest manner by using different housing-like shells. For example, the housing-like shell that contains the electronic circuit can be of a different color than the shell without electronic circuit, so that the user can clearly see which injection device is the one with the instructions.

In an advantageous design, the injection device comprises a device for service life monitoring or for monitoring the expiration date of the drug. Such a monitoring device makes sense for drugs that have a limited shelf life and that should no longer be administered after a certain storage time. In addition, such a monitoring device can comprise a temperature monitoring that notifies the user when there is a risk that the drug could be damaged due to thermal impact. The structure and the function of the device are described below. In the following example, which is kept simple, two fastening points are connected via an electrical conductor. The holding devices that are attached to the described fastening points have electrically conductive areas. These areas of the holding devices contact the electrical conductor. The electrically conductive areas in turn are connected in a conductive manner to electronic assemblies arranged on the inner side of a housing-like shell. The electronic assemblies form an electronic circuit. When the shell is applied to the housing, the conductive areas on the two holding devices are electrically connected by the conductor. As a result, another battery arranged on the housing-like shell can be activated. Consequently, the electronic assemblies can be supplied with energy, as a result of which, in particular, a timer is started. The electronic assemblies are moreover connected to display elements, which can be seen or felt on the external side of the housing-like shells. The display elements can be simple LEDs; however, it would also be conceivable to use a display or an acoustic signal giver. Thus, the timer is activated at the time of the final mounting of the injection device. In the present example, the timer can be set to a certain number of months, in accordance with the expiration date of the drug. After the expiration of the time limit of the timer, the electronic circuit generates a signal that is supplied to the display elements. In the case of LEDs as display elements, these LEDs can start to light up and thus signal to the user that the injection device should no longer be used. Additionally, the electronic circuit can be provided with a temperature sensor. By means of this temperature sensor, the temperature within the injection device can be monitored. If the temperature within the injection device exceeds a certain value for a certain duration, so that it can be assumed that the drug has been damaged, then the electronic circuit generates a signal that is supplied to the display element. For example, the same LEDs as those used when the expiration date has been reached can also be used and thus warn the user against actual use. Alternatively, other display means can also be used for the temperature warning. In addition, this design can also optionally comprise an electromechanical actuator, e.g., with a cotter pin (see also above), that blocks the injection device in the case of a temperature warning.

As described, the connection between the housing-like shells and the housing should be non-detachable in an injection device according to the invention. If electronic components and, in any case, energy storages are arranged on the housing-like shells, then it can be advantageous if the housing-like shells have openings or predetermined breaking points that enable the removal of the shells, for example, by means of special tools, for correct disposal or recycling of the electronics and any energy storage present. Here it is advantageous if the disengagement of a shell from the housing leaves visible traces on the shell, so it can be seen clearly that the shell has already been used. Advantageously, after disengagement, the shell falls apart into multiple fragments. Alternatively, at the time of the disengagement, a seal can also be broken or holes can form on the shell.

In preferred designs of the housing-like shell, the shells are made of plastic, in particular by the injection molding process. In advantageous designs, the housing shells can be so-called two-component parts that are made of two plastics having different properties, for example, different hardnesses, which can advantageously influence the haptics of the shells. A design with two-component parts, in which two plastics of different hardness are used, can be designed such that the area of the shells that the user uses as handle has the softer material on the surface in order to allow a comfortable and reliable holding experience. The soft component can also be used, additionally or exclusively, on the inner side of the shells and then be used as mechanical damping material with respect to the housing, or, as a result of potential resilient or plastic deformability/shape adaptation, it can be used to eliminate play between the housing and shells.

In another interesting design, the housing-like shells can comprise bulk material, liquid- or gel-filled cushions which adjust their shape, for example, to the hand of the user. As bulk material, sand, millet, bran or plastic particles can be used. As examples of liquids, water or oils, in particular silicon oils, are mentioned in particular. As gels, biopolymer gels, particularly gelatin or agar, or silicon-based gels are indicated.

In additional designs, the housing-like shells can have other functional features. Thus, the shells can comprise shock-absorbing elements, elements that prevent adulteration, particularly holograms, printed signs or codes, particularly QR codes, or molded-on signs or codes, particularly using the Braille script. Moreover, the shells can have temperature-sensitive coatings, or they can be constructed from temperature-sensitive plastics that reversibly or irreversibly change their color depending on the temperature.

The housing shells can also comprise decorative elements, such as paints and added-on shapes, for example, symbols, animal figures or cartoon characters. These decorative elements can protrude or project three-dimensionally from the shell.

In another embodiment, the injection device comprises a group of more than two housing-like shells, in particular, three or four shells, which can be attached as a group to the housing in a non-detachable manner. Here, a holding device of a first shell can be blocked by a blocking device of a second shell on the housing. A holding device of the second shell can then be blocked by the blocking device of a third shell on the housing and so on. Here, it is also possible that the holding and blocking devices are arranged on the shells in reversed order and that a plurality of holding and blocking devices engage in one another between two shells, if the shells are attached to the housing. Finally, the last shell in a group of shells for an injection device can close the circumference around the housing and engage together with the first shell, fastening the group of shells definitively and in a non-detachable manner to the housing.

The holding devices themselves on the shells are advantageously designed in advantageous embodiments of the invention as snap arms, at the free end of which typically a tooth-like structure is arranged, which can lock into a shape complementary thereto on fastening points of the housing. Alternatively, instead of a tooth-like structure, an opening can also be provided on the snap arms, which can lock into a tooth-like structure at fastening points of the housing. These embodiments have in common that, for disengaging the locking, a deflection of the snap arm relative to the housing is necessary. In embodiments according to the invention, this deflection is prevented by the blocking device, which is configured as a rib, beam, wedge or projection on the respective shell. Here, the exact shape of the blocking device is less important than its spatial arrangement on the respective shell, which has to be selected in such a manner that it can prevent the disengagement of the locking.

In another embodiment, for the attachment of the shells, an adhesive connection between fastening point, holding device and/or blocking device can also be established. This is possible using adhesives that are suitable for the respective materials used. Another possible design consists in that, between holding device and fastening device, there is no actual locking, but a purely adhesive, soldering or welding connection is established, which is broadened onto the blocking device. Furthermore, it would also be possible to use screw, crimp or riveting connections.

The person skilled in the art can immediately and obviously recognize additional embodiments and designs that result from combinations of the described examples or combinations of the described examples with the general technical knowledge of the person skilled in the art. The examples listed here and also below are meant to indicate basic possibilities of the invention and should in no way be interpreted to be limiting. Moreover, any of the components of the designs described herein may be excluded and therefore the designs may be free of certain components described herein.

BRIEF DESCRIPTION OF THE DRAWINGS

FIG. 1: an exploded view of an autoinjector according to a possible design.

FIGS. 2a-2c: the autoinjector from FIG. 1 in a delivery state, wherein FIGS. 2a to 2c are cross-sectional views extending through the longitudinal axis of the device, wherein the cross-sectional views are angularly offset about the longitudinal axis.

FIGS. 3a-3c: the device and the views from FIGS. 2a-2c, wherein a needle protection sleeve is in its actuated position.

FIGS. 5a-5c: the device and the views from FIGS. 2a-2c, wherein a driving element is shown at the end of its discharge stroke.

FIGS. 6a-6c: the device and the views from FIGS. 2a-2c, wherein a signal that indicates the end of the product discharging is generated.

FIGS. 7a-7c: the device and the views from FIGS. 2a-2c, wherein the needle protection sleeve is in its needle protection position.

FIGS. 8a-8d: perspective views of a multipart syringe holder according to a first variant.

FIGS. 9a-9c: perspective views of a syringe holder according to a second variant.

FIGS. 11a-11c: perspective views of a syringe holder according to a fourth variant.

FIGS. 12a-12c: perspective views of a syringe holder according to a fifth variant.

FIGS. 8e, 9d, 10e, 11d, 12d: longitudinal sections of the five variants in the delivery state and, for the second to fifth variant, in a respective position with partially and completely inserted syringe.

FIG. 13: perspective view of an autoinjector with a housing-like shell according to an embodiment according to the invention, wherein features of the autoinjector substantially correspond to the autoinjector from FIG. 1.

FIGS. 14a-14b: cross sections through an embodiment of the injection device according to the invention, wherein FIG. 14b shows only the housing-like shells.

FIG. 15: perspective detail view of an embodiment according to the invention.

FIG. 16: perspective detail view of an additional embodiment according to the invention.

FIGS. 20a-20c: three-dimensional views of an injection device according to the invention with four housing-like shells.

FIGS. 21a-21b: cross section and cross-sectional details of the injection device from FIGS. 20a-c.

FIGS. 23a-23e: housing-like shell with electronics module.

FIGS. 24a-24b: detail views of the electronics module.

DETAILED DESCRIPTION

Figure 4A:
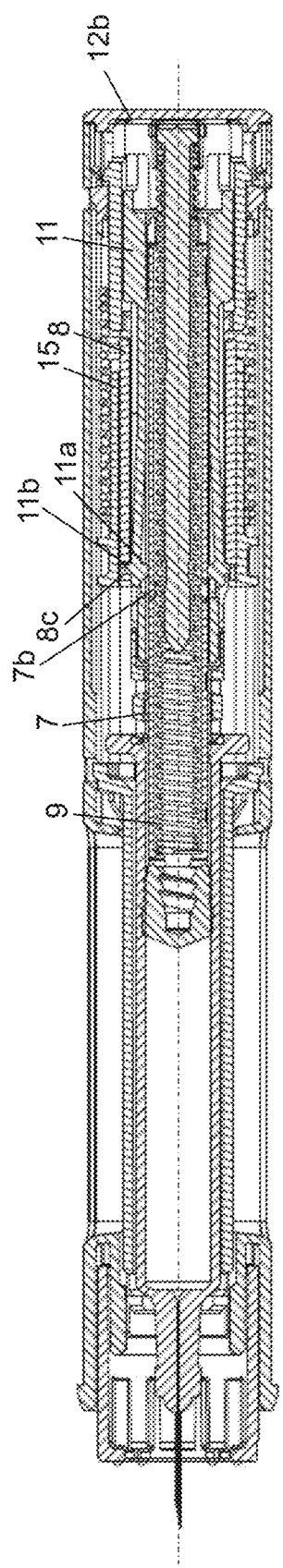
FIGS. 4a-4c: the device and the views from FIGS. 2a-2c, wherein the driving element is shown at the end of a first partial stroke of its discharge stroke.
Figure 4B:
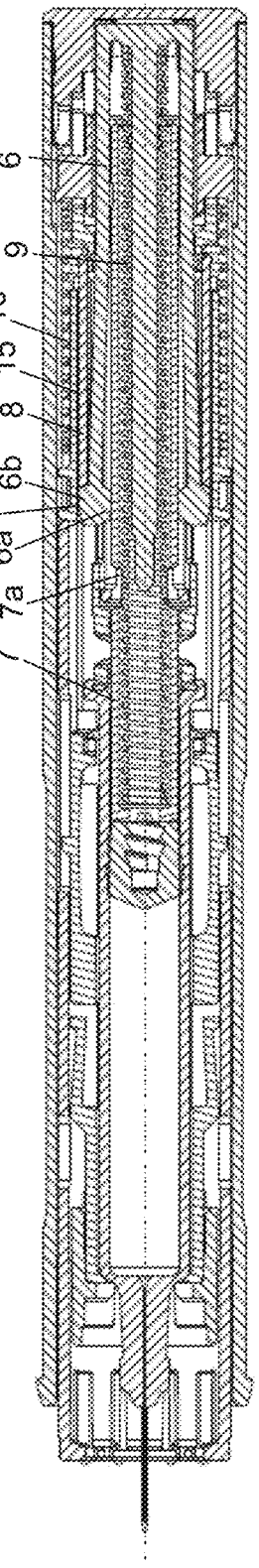

Below, preferred forms of an injection device are described, for which the invention could be used, in particular, autoinjectors. This description should in no way be interpreted to be limiting; instead, it should only be considered to be a possible design. Thus, the invention could also be used on other injection devices such as, for example, the ServoPen from the company Ypsomed or the FlexPen from the company Novo Nordisk.

In reference to FIGS. 1-7c, the structural features and the function of the example autoinjector will now be described.

The autoinjector, as shown in FIG. 1, for example, comprises a sleeve-shaped, elongated housing 2 with a longitudinal axis L, which comprises a closure cap 12 at its proximal end and which is connected by positive locking to the housing 2 in a rotationally and axially fixed manner and which forms the proximal end of the autoinjector. The closure cap 12 is snapped to the housing 2. For this purpose, the closure cap 12 comprises a locking element 12a that locks into a recess 2a on the housing 2, preferably in such a manner that the closure cap 12 is not detachable or not readily detachable from the housing 2.

At the distal end of the autoinjector, in its delivery state (FIGS. 2a-2c), a pull-off cap 4 is arranged, which is pulled off or twisted off before the use of the injector, and removed.

In the housing 2, a product container 13 in the shape of a syringe is accommodated in a manner such that it cannot be shifted along the longitudinal axis L with respect to the housing 2, except for the mounting of the autoinjector. The product container 13 comprises a sleeve-shaped syringe body, which surrounds a piston 13b in a sealing manner on the inner circumference of the syringe body, the piston being in sealing contact on the inner circumference of the syringe body. At its distal end, the syringe body comprises an injection needle 13a, which is connected, in particular in a non-detachable manner, to the syringe body, and the distal end of which is formed by the needle syringe. Between the injection needle 13a and the piston 13b, a liquid product, in particular a drug, is arranged within the syringe body, wherein, as a result of shifting the piston 13b in a discharge direction, i.e., in the distal direction or toward the injection needle 13a, the liquid product is discharged through the hollow injection needle 13a from the product container 13. At its proximal end, the syringe body has a so-called finger flange that protrudes radially outward over the outer circumference of the cylindrical syringe body.

The product container 13 is accommodated in a product container holder, which is referred to as syringe holder 1, so that it is secured at least against a movement along the longitudinal axis L in the distal direction relative to the syringe holder 1. The syringe holder 1, as can be seen best from FIG. 2a, is connected, in particular locked by positive locking, to the housing 2. For this purpose, the housing 2 has recesses into which the locking elements formed here at the proximal end of the syringe holder 1 engage. The syringe holder 1 has at least one inward protruding shoulder 1b, against which a tapering section of the product container 13, namely the distal section of the cylindrical syringe body section that guides the piston 13b, is braced.

In order to prevent that the product container 13 can be shifted relative to the syringe holder 1 in the proximal direction, the product container 13 is pressed at its proximal end by a holder acting on the syringe body into engagement with the shoulder 1b. The holder is formed by a holding spring section 5c of a mechanism holder 5. In particular, the mechanism holder 5 is arranged in such a manner that it cannot be shifted and/or is rotationally fixed relative to the housing 2 along the longitudinal axis L. The sleeve-shaped mechanism holder 5 can be snapped to the housing 2. By means of the holding spring section 5c, differences in length of the product container 13, which can arise due to manufacturing tolerances, can be compensated for, wherein the firm seat of the product container 13 on the shoulder 1b is ensured.

The product container 13 is arranged relative to the housing 2 in such a manner that the needle tip projects distally over the distal end of the housing 2. In the starting or delivery state of the autoinjector, i.e., when the pull-off cap 4 is arranged on the autoinjector, the needle 13$a$ is covered by a needle cover cap 14, which, in the example shown, is configured as a so-called rigid needle shield known to the person skilled in the art, alternatively as a soft needle shield, in order to protect the needle 13$a$ against soiling, or to keep the needle 13$a$ and the drug sterile. The rigid needle shield 14 is arranged on a needle holding section of the syringe body, wherein the tapering section of the syringe body is located between the needle holding section and the cylindrical section of the syringe body. The shoulder 1$b$ is arranged between the syringe body and the proximal end of the rigid needle shield 14, in particular in such a manner that a gap, albeit a small gap, is formed between the rigid needle shield 14 and the shoulder 1$b$, in order to prevent the shoulder 1$b$ from exerting a force on the rigid needle shield 14, as a result of which, for example, the sterility of the needle 13$a$ or of the liquid product could be impaired. The pull-off cap 4 is detachably snapped to the housing 2 or a needle protection sleeve 3, wherein this snap connection is disengaged when the pull-off cap 4 is removed from the housing 2 or the needle protection sleeve 3. In the example shown, the snap connection is produced by a snap geometry 3$b$ of the needle protection sleeve 3 and a snap hook 4$a$ of the pull-off cap 4 (FIG. 2$b$). These snap hooks 4$a$ further secure the pull-off cap 4 against a proximal movement relative to the housing 2, in that they find a housing-fixed bracing on the housing 2 and/or on a distal front side on the syringe holder 1. Furthermore, the pull-off cap 4 comprises, in particular on a snap hook 4$a$, at least one snapper 4$b$ that engages in a gap between the syringe body, in particular its tapering area, and the proximal end of the rigid needle shield 14. When the pull-off cap 4 is removed from the autoinjector, the snapper 4$b$ snaps into the proximal end of the rigid needle shield 14, as a result of which the rigid needle shield 14 is disengaged from the product container 13 and removed together with the cover cap 4 from the autoinjector.

The autoinjector comprises a needle protection sleeve 3 that can be shifted relative to the housing 2 and along the longitudinal axis L by an actuation stroke $H_B$ in the proximal direction into an actuated position, in order to trigger a product discharge. In the starting position of the needle protection sleeve 3, as shown in the FIGS. 2$a$-2$c$, wherein the pull-off cap 4 has been removed, the distal end of the needle protection sleeve 3 projects distally over the needle tip of the needle 13$a$, so that access to the needle tip is at first prevented. By shifting the needle protection sleeve 3 by the actuation stroke $H_B$, the needle protection sleeve 3 is shifted sufficiently in the proximal direction that the needle 13$a$ exits from the distal end of the needle protection sleeve 3, in particular by a length corresponding to the depth of injection of the needle at the puncture site. Preferably, the needle 13$a$ should project sufficiently over the distal end of the needle protection sleeve 3 such that a subcutaneous injection can occur. In particular, the housing 2 can form an abutment 2$c$ with which the needle protection sleeve 3 is in contact in the actuated position.

After the injection has occurred, the needle protection sleeve 3 can be shifted relative to the housing 2 from the actuated position along the longitudinal axis L by a needle protection stroke $H_N$ in the distal direction into a needle protection position (FIGS. 7$a$-7$c$). In the needle protection position, the distal end of the needle protection sleeve 3 projects distally over the needle tip, so that access to the needle tip is prevented and the risk of injury is reduced. As described further below, the needle protection sleeve 3 can be blocked against renewed shifting back out of the needle protection position.

The syringe holder 1 comprises a radially outward pointing protrusion 1$a$, wherein the protrusion 1$a$ engages in a slot-shaped recess of the needle protection sleeve 3, which is arranged between the housing 2 and the syringe holder 1. In the starting position of the needle protection sleeve 3 (FIGS. 2$a$-2$c$) and/or in the needle protection position of the needle protection sleeve 3 (FIGS. 7$a$-7$c$), the needle protection sleeve 3, in particular the proximal end of the slot-shaped recess, is in contact with the protrusion 1$a$, as a result of which a movement of the needle protection sleeve 3 in the distal direction is prevented. A cam 1$c$, which is arranged resiliently on the syringe holder 1 and formed by the syringe holder 1, can engage into this slot-shaped recess or alternatively into another recess of the needle protection sleeve 3. The cam 1$c$ is configured such that, when an attempt is made to shift the needle protection sleeve 3 from the starting position into the actuated position, the cam 1$c$ at first prevents the shifting of the needle protection sleeve 3, wherein the cam 1$c$ is pushed out, if the force exerted onto the needle protection sleeve 3 for backward shifting exceeds a certain threshold value, as a result of which the needle protection sleeve 3 is abruptly shifted into the actuated position. As a result, the needle 13$a$ can be stuck abruptly in the puncture site. For the sticking of the needle 13$a$ or for the shifting of the needle protection sleeve 3 into the actuated position, the distal end of the needle protection sleeve 3 is placed on the puncture site, wherein the housing 2 is then pressed in the direction of the puncture site, wherein, when the pressure force exceeds the above-mentioned threshold value, the housing 2 is abruptly shifted toward the puncture site and the needle protection sleeve 3 is shifted relative to the housing 2 into the actuated position.

The housing 2 has a ring-shaped holding section or ring section 2$b$ which, in particular, surrounds the distal end of the syringe holder 1, particularly in the shape of a ring, and which is in contact with said distal end, as a result of which the at least one shoulder 1$b$ is held in engagement with the tapering area of the syringe body. Furthermore, in the area of the holding section 2$b$, the housing 2 has a translation abutment in the shape of a holding shoulder 2$e$, which prevents the syringe holder 1 from being shifted relative to the housing 2 in the distal direction, if the syringe holder 1 is in contact with the holding shoulder 2$e$. This also applies advantageously to the described variants.

The autoinjector moreover has a sleeve-shaped driving element 7, which, on its distal end, forms an inward protruding shoulder against which a first spring 9, which can also be referred to as discharge spring, is braced. The first spring 9 is arranged within the sleeve-shaped driving element 7. The first spring 9 is a coil spring acting as a compression spring, which, in the starting or delivery state of the autoinjector, is pre-stressed with sufficient energy so that it can discharge the product contained in the product container 13, in particular completely, by shifting the driving element 7 by a discharge stroke $H_A$ out of the product container 13. In the delivery state of the device, a spacing exists between the piston 13$b$ and the distal end of the driving element 7, so that the driving element 7 abuts only during the performance of the discharge stroke $H_A$ against the piston 13$b$ and drives said piston in the discharge direction.

The first spring 9 is braced with its proximal end against a holding element 6 which, in this example, has two arms 6$c$, wherein, on each arm 6$c$, a first engagement element 6$a$ and a second engagement element 6b are arranged. The first engagement element 6a points radially toward the longitudinal axis L, wherein the second engagement element 6b points radially away from the longitudinal axis L. The first engagement element 6a engages in a first recess 7a that is formed by the driving element 7, as a result of which a movement of the driving element 7 relative to the holding element 6 in the distal direction or in the discharge direction is prevented. As a result, the first spring 9 is held in its stressed state. The holding element 6 comprises a guide pin 6d that is inserted through the proximal end of the first spring 9 into the core of the first spring 9. The guide pin 6d prevents a lateral buckling of the first spring 9 during and at the end of the discharge stroke $H_A$ of the driving element 7.

The autoinjector comprises a switching module 8, 15, which comprises a switch sleeve 15 and a blocking sleeve 8 surrounded by the switch sleeve 15. In the delivery state of the device, the first engagement element 6a is held by the inner circumference of the blocking sleeve 8, which is in contact with the second engagement element 6b, in engagement with the first recess 7a.

The switch sleeve 15 is connected to the proximal end 3a of the needle protection sleeve 3 or it is at least in contact with the proximal end 3a of the needle protection sleeve 3. A second spring 10, within which the first spring 9 is arranged and which preferably surrounds the switch sleeve 15 and the blocking sleeve 8 at least partially, is braced with its distal end against the switch sleeve 15. A portion of the switch sleeve 15 is thus arranged between the needle protection sleeve 3 and the distal end of the second spring 10. The second spring 10 is a spring made of metal that acts as a compression spring and is configured as a coil spring. The second spring 10 is braced with its proximal end against a signal element 11, in particular against a protrusion 11c, which engages in the housing 2 such that it can be shifted axially and is rotationally fixed, and which extends through a slot-shaped groove 5b of the mechanism holder 5. The second spring 10 thus also surrounds the mechanism holder 4 at least partially, preferably completely.

The switch element 15 has a recess 15a, into which a locking element 8a of the blocking sleeve 8 engages. The locking element 8a is in the shape of a sawtooth and protrudes radially away from the longitudinal axis L. The locking element 8a is arranged resiliently on an arm that is formed by the blocking sleeve 8. Due to shifting of the switch sleeve 15 in the proximal direction, the blocking sleeve 8 is driven via the engagement of the locking element 8a in the proximal direction.

Due to shifting of the needle protection sleeve 3 into the actuated position, the switch sleeve 15 is also driven by the actuation stroke $H_B$, as a result of which the second spring 10 is stressed. If the needle protection sleeve 3 is not shifted completely into the actuated position, the second spring 10 can shift the switching sleeve 15 and the needle protection sleeve 3 again back into the starting position, wherein, via the engagement of the locking element 8a, the blocking sleeve 8 is also driven by the switch sleeve 15.

The signal element 11, which, in particular, is in the shape of a sleeve in the delivery state or before the triggering of the product discharge, is in an axially fixed engagement with the driving element 7. The signal element 11 comprises a first engagement element 11a that engages in a recess 7b of the driving element 7 and that comprises a second engagement element 11b. The first engagement element IIa and the second engagement element 11b are arranged resiliently on the end of an arm 11d. The signal element 11 has two such arms 11d with a first engagement element 11a and a second engagement element 11b. The first engagement element 11a points radially toward the longitudinal axis L, wherein the second engagement element 11b points radially away from the longitudinal axis L. In the delivery state, the first engagement element 11a is held by the inner circumference of the blocking sleeve 8 in axially fixed engagement with the driving element 7. The second engagement element 11b is in contact with the inner circumference of the switch sleeve 8. The closure cap 12 has a signal abutment 12b, against which the signal element 11 can abut for the generation of a signal and with which the signal element 11 is preferably in contact in the delivery state of the device.

For the administration of the product from the product container 13, the pull-off cap 4 is removed from the autoinjector together with the rigid needle shield 14. The distal end of the needle protection sleeve 3 is placed on the puncture site of a patient, wherein the housing 2 is shifted toward the puncture site, as a result of which the needle protection sleeve 3 is moved from its starting position by the actuation stroke $H_B$ in the proximal direction relative to the housing 2 into the actuated position. As a result, the second spring 10 is stressed, wherein the switch sleeve 15 is driven by the needle protection sleeve 3 by the actuation stroke $H_B$. The blocking sleeve 8 has a first recess 8b which, by shifting of the blocking sleeve 8 by the actuation stroke $H_B$, is moved along the longitudinal axis L to the position of the second engagement element 6b, as represented in FIGS. 3a-3c. As a result, the first engagement element 6a is moved out of the engagement with the driving element 7 with a movement transverse to and away from the longitudinal axis L, wherein, at the same time, the second engagement element 6b is moved into engagement with the blocking sleeve 8, in particular its first recess 8b. As a result, the driving element 7 is unlocked for the movement by the discharge stroke $H_A$ in the discharge direction.

Since the axially fixed coupling between the driving element 7 and the holding element 6 is now disengaged, the holding element 6, which can be moved at least by some distance relative to the housing 2 and along the longitudinal axis L, can be moved by the first spring 9 in the proximal direction, wherein, via the engagement of the second engagement element 6b in the recess 8b, the holding element 6 drives the blocking sleeve 8 by a start signal stroke $H_K$ (FIG. 3c), as a result of which the blocking sleeve 8 abuts against a start signal abutment 5a, which is formed by the mechanism holder 5, and thereby outputs an acoustic and/or tactile signal that signals to the user of the device that the product discharge has started. Due to the shifting of the blocking sleeve 8 by the actuation stroke $H_B$, the locking element 8a is unlocked for a movement transverse to and toward the longitudinal axis L, since the mechanism holder 5 has an indentation 5d that allows such a movement of the locking element 8a if the blocking sleeve 8 has been shifted by the actuation stroke $H_B$ or if the needle protection sleeve 3 is in its actuated position.

Figure 4C:
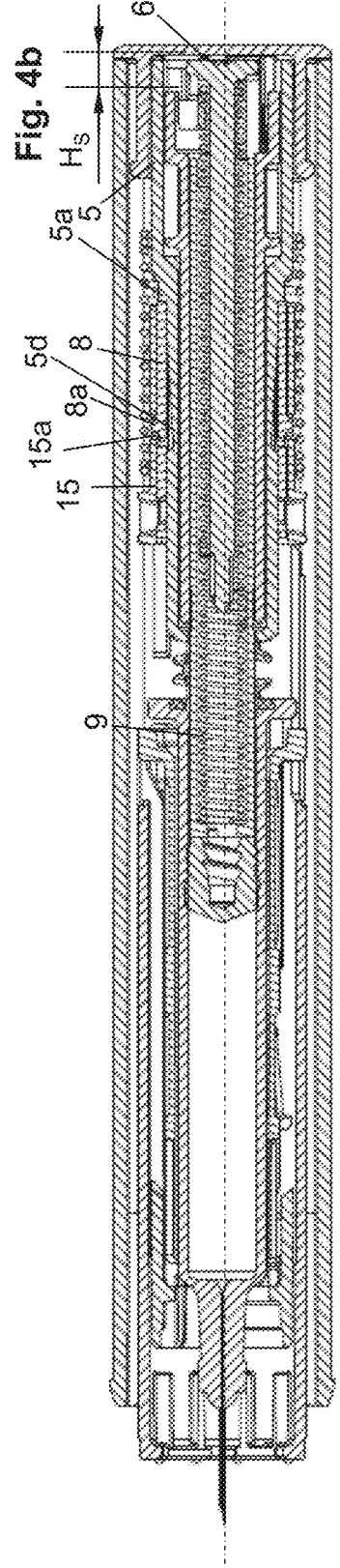

Since the signal element 11 is still connected in an axially fixed manner to the driving element 7, it is driven by a first partial stroke Hs of the discharge stroke $H_A$ in the discharge direction, wherein the signal element 11 is moved approximately by the first partial stroke Hs away from the signal abutment 12b, as can be seen best from FIG. 4c. At the end of the first partial stroke Hs, while the first and second engagement elements 11a, 11b are moved relative to the blocking sleeve 8, the first engagement element 11a is pressed out of the engagement with the driving element 7, wherein, at the same time, the second engagement element 11b is moved into the second recess 8c of the blocking sleeve 8 with a movement transverse to the longitudinal axis L and radially away from the longitudinal axis L. As a result, the signal element 11 is prevented from moving in the proximal direction relative to the housing 2 or the blocking sleeve 8. The second engagement element 11*b* is held by the outer circumference of the driving element 7 in engagement with the recess 8*c* (FIG. 4*a*) if the driving element 7 is moved by its second partial stroke of the discharge stroke $H_A$. The outer circumferential surface of the driving element 7 holds the second engagement element 6*b* in engagement with the first recess 8*b* of the blocking sleeve 8, as can be seen best from FIG. 4*b*. At the end of the discharge stroke $H_A$, the driving element 7 unlocks the second engagement element 11*b* from the engagement with the blocking sleeve 8, as a result of which the second engagement element 11*b* is moved out of the engagement with the recess 8*c*, in particular toward the longitudinal axis L, so that the second spring 10 accelerates the signal element 11 against the discharge direction, i.e., in the proximal direction, so that, when the signal element 11 abuts against the signal abutment 12*b*, an acoustic and/or tactile signal is generated.

As can be seen best from FIG. 5*b*, the engagement of the second engagement element 6*b* in the first recess 8*b* persists, as a result of which a movement of the blocking sleeve 8 in the distal direction relative to the housing 2 is prevented.

Due to the removal of the autoinjector from the injection site, the second spring 10 can move the switch sleeve 15 and the needle protection sleeve 3 from the actuated position into the needle protection position by the needle protection stroke $H_N$, wherein the locking element 8*a* is pressed out of the engagement with the recess 15*a*, wherein the switching sleeve 15 is moved relative to the blocking sleeve 8 in the distal direction. When the needle protection sleeve 3 is in its needle protection position, the locking element 8*a* snaps to the switch sleeve 15, wherein the locking element 8*a* prevents the needle protection sleeve 3 from being shifted back into its actuated position. When an attempt is made to shift the needle protection sleeve 3 from the needle protection position back into the actuated position, the switch element 15 abuts against the locking element 8*a*, which prevents the movement of the needle protection sleeve 3 into the actuated position. For this purpose, the blocking sleeve 8 is braced axially against the start signal abutment 5*a* of the mechanism holder 5.

Below, different embodiments of a syringe holder are shown, which can be used in an autoinjector, but preferably not necessarily an autoinjector of the type described above.

The injection module from FIGS. 8*a* to 8*d* comprises a first shell body or sleeve body 103 that has an opening laterally and at least one shoulder-shaped engagement element, i.e., in the example shown, two shoulder-shaped engagement elements 1*b* that protrude inward, i.e., toward the longitudinal axis of the sleeve body 103. Furthermore, the sleeve body 103 comprises a translation counter-abutment 1*k* pointing in the distal direction. For the mounting of the syringe 13 (FIG. 8*b*), said syringe is inserted laterally, i.e., with a movement transverse to the longitudinal axis into the sleeve body 103, as a result of which the at least one engagement element 1*b* is inserted in the gap between the needle protection cap 14 and the tapering section of the syringe body of the syringe 13.

Furthermore, the injection module comprises a second shell body, in particular a sleeve body 104 (FIG. 8*c*), which is open at its proximal end and which comprises at its distal end at least one translation abutment, i.e., in the example shown, two translation abutments 1*m* that protrude radially inward. As in the design from FIGS. 1 to 7*c*, the sleeve body 104 comprises a cam 1*c*, namely two cams 1*c* and at least one protrusion 1*a*, namely two protrusions 1*a*. The cam 1*c* is arranged resiliently via an arm on the sleeve body 104.

The unit consisting of syringe 13, needle protection cap 14 and the first sleeve body 103 is inserted over the proximal end along the longitudinal axis with the needle protection cap 14 first (FIG. 8*b*) into the second sleeve body 104 (FIG. 8*c*), wherein the translation counter-abutment 1*k* abuts against the translation abutment 1*m* if the unit 13, 14, 103 is inserted completely into the sleeve body 104 (FIG. 8*d*). The unit shown in FIG. 8*d* is then shifted for mounting in such a manner in the housing 2 of the autoinjector that the holding section 2*b*, in particular the ring-shaped holding section or ring section, adjoins at least the first sleeve body 103 at least in the area of the engagement element 1*b*, so that the engagement element 1*b* is held in engagement with the tapering section of the syringe body. Furthermore, the holding section 2*b* can also adjoin the second sleeve body 104, particularly in the area on which the at least one translation abutment 1*m* is formed, in order to keep the translation abutment 1*m* in engagement with the translation counter-abutment 1*k*.

In the embodiment shown in FIGS. 9*a*-9*c*, the syringe module, in particular the syringe holder, comprises a first shell body 101 and a second shell body 102, each of which is formed as semi-shell. Each shell body 101, 102 comprises a cam 1*c* and a protrusion 1*a* in the manner described herein.

The first shell body 101 and the second shell body 102 are connected to one another over several predetermined breaking points in such a manner as to form a single part in the view shown in FIG. 9*a*, wherein the first and second shell bodies 101, 102 assume an insertion position with respect to one another. Via the proximal end of the body 101, 102 shown in FIG. 9*a*, the syringe 13 is inserted with the needle protection cap 14 first in the distal direction (FIG. 9*b*), until the gap between the tapering section and the needle protection cap 14 is arranged along the longitudinal axis L in the same position as the at least one engagement element 1*b*. In the example shown, each of the first and second shell bodies 101, 102 comprises an engagement element 1*b*. Due to the fact that the first and second shell bodies 101, 102 are pressed against one another transversely to the longitudinal axis L, the predetermined breaking points break, wherein the first and second shell bodies 101, 102 engage in one another with positive connection, and the engagement elements 1*b* are moved into the gap. As already described, the area of the first and second shell bodies 101, 102 on which the engagement element 1*b* is formed can be bordered by the holding section 2*b* of the housing 2, as a result of which the engagement elements 1*b* are held in engagement with the tapering area of the syringe body. Particularly preferably, when the syringe 13 is inserted, the shell bodies 101, 102 can move transversely to the longitudinal axis, against the resilient force of the arms that carry the protrusion 1*a* and/or the cam 1*c*, into the insertion position. Subsequently, as described, the engagement elements 1*b* here too can be brought and held in engagement with the tapering section of the syringe body 13 by the holding section 2*b* of the housing 2. Alternatively or additionally, the first shell body 101 and the second shell body 102 can lock into one another in the closed position (FIG. 9*c*), in which the engagement elements 1*b* engage in the gap.

In the design shown in FIGS. 10*a*-10*d*, the syringe holder 1 comprises a first shell body 101 and a second shell body 102, which are each formed as a semi-shell and, in particular, designed to be identical to allow a saving of tool costs.

Each of the first and second shell bodies 101, 102 has a cam 1c and a protrusion 1a in the described manner. Furthermore, each of the first and second shell bodies 101, 102 comprises an engagement element 1b at its distal end.

Figure 10B:
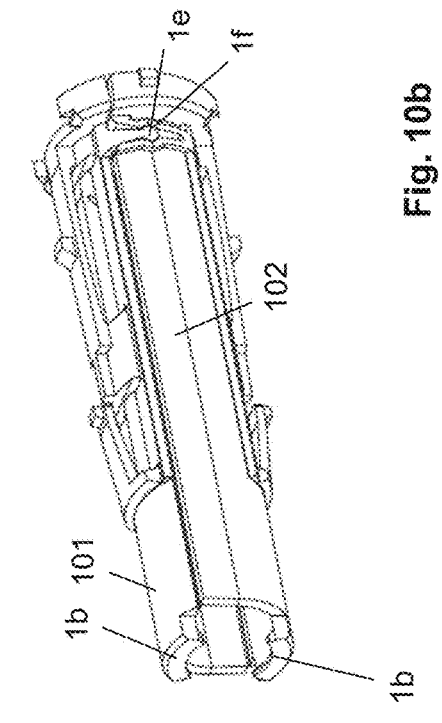
FIGS. 10a-10d: perspective views of a syringe holder according to a third variant.
Figure 10D:
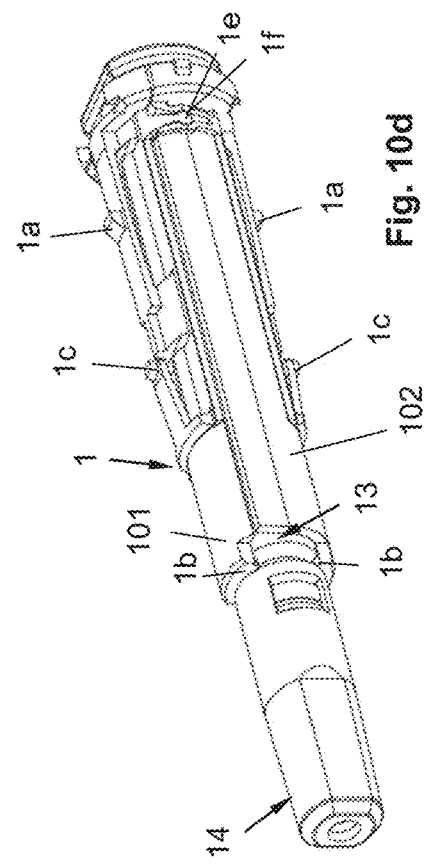
Figure 10A:
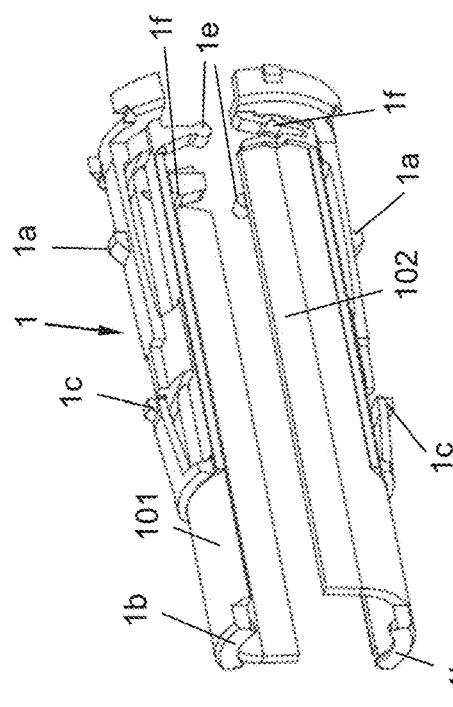
Figure 10C:
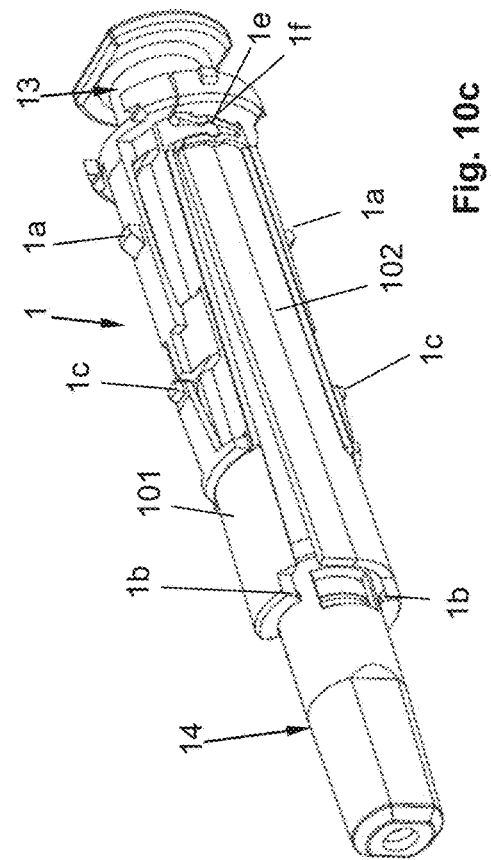

Each of the shell bodies 101, 102 comprises a hinge pin 1e and a hinge pin accommodation 1f (FIG. 10a), wherein the hinge pin 1e of one shell body 101, 102 is inserted in the hinge pin accommodation 1f of the other shell body 102, 101 (FIG. 10b), so that the first and second semi-shells 101, 102 can be pivoted relative to one another about the pivot axis of the pivot joint 1e, 1f that is formed by the hinge pins 1e and the hinge pin accommodations 1f, namely between an insertion position (FIG. 10c) and a closing position (FIG. 10d). The syringe 13 together with the needle protection cap 14 is inserted over the proximal end of the syringe body 1, wherein the needle protection cap 14 is moved past the engagement element 1b, wherein the first shell body 101 and the second shell body 102 are pivoted toward one another if the gap between the needle protection cap 14 and the tapering area of the syringe body is in the same position relative to the longitudinal axis L as the engagement elements 1b. As a result, the engagement elements 1b engage in the mentioned gap. As described, the engagement elements 1b can be held by the holding section 2b of the housing 2 in engagement with the tapering section of the syringe body. Alternatively or additionally, the first shell body 101 and the second shell body 102 can be locked to one another in the closing position (FIG. 10d), in which the engagement elements 1b engage in the gap.

In FIGS. 11a to 11c, a design form of the syringe holder 1 is shown that comprises a first sleeve body 103 and two pivot arms 1h. The protrusion 1a is formed on the sleeve body 103. For each of the pivot arms 1h, the sleeve body 103 forms two hinge pin accommodations 1g, in which, in each case, a hinge pin 1i of the pivot lever 1h is arranged. Each of the pivot levers 1h forms two hinge pins 1i that are locked to the hinge pin accommodation. The hinge pin 1i is rotatable relative to the hinge pin accommodation 1g and can slide on the hinge pin accommodation 1g. The pivot lever 1h comprises a lever section that points in the distal direction, wherein, at the distal end of this lever section, the engagement element 1b formed by the pivot 1h is formed for engagement in the gap between the needle protection cap 14 and the tapering section of the syringe body.

The pivot lever 1h shown in the example is two-armed, wherein the lever section, which projects from the pivot joint 1g, 1i in the direction opposite the direction of the arm forming the engagement element 1b, forms the cam 1c.

The syringe 13 is introduced with the needle protection cap 14 first over the proximal end of the sleeve body 103 into the sleeve body 103, wherein the needle protection cap 14 is moved past the engagement elements 1b, until the gap between the tapering area of the syringe body and the needle protection cap 14 relative to the longitudinal axis is located in the same position as the engagement elements 1b. Due to the pivoting of the pivot lever 1h, the engagement elements 1b are pivoted into the gap or toward the longitudinal axis. The unit shown in FIG. 11c is then arranged in the housing 2 of the autoinjector in such a manner that the holding section 2b fixes the pivot lever 1h in such a manner that the engagement elements 1b are held in engagement with the tapering section of the syringe body. The arm on which the cam 1c is formed is resiliently deformable relative to the arm on which the engagement element 1b is formed, as a result of which the cam 1c can perform the intended task with regard to the needle protection sleeve 3. In particular, the cam 1a is used as an abutment for the needle protection sleeve 3, wherein the needle protection sleeve 3 adjoins the cam 1a if the needle protection sleeve is in its starting position and/or in its needle protection position.

In a fifth design form shown in FIGS. 12a-12d, the syringe module, in particular the syringe holder 1, comprises a sleeve body 103. The sleeve body 103 comprises, in particular, two cams 1c, and, in particular, two protrusions 1a in the manner shown here.

In this variant, the at least one engagement element can be formed resiliently as shoulder 1b, in particular on a resilient arm 1h, on the syringe holder, wherein the syringe 13 is inserted over the proximal end with the needle first into the syringe holder, which is preferably sleeve-shaped, wherein the needle protection cap 14 deflects the at least one engagement element 1b transversely to the longitudinal axis outward, i.e., away from the longitudinal axis, wherein, if the needle protection cap 14 has been moved completely past the at least one engagement element 1b, the at least one engagement element 1b snaps in the gap between the tapering area of the syringe 13 and the proximal end of the needle protection cap 14. The unit shown in FIG. 12c is then arranged in the housing 2 of the autoinjector in such a manner that the holding section 2b fixes the arm 1h so that the engagement elements 1b are held in engagement with the tapering section of the syringe body 13 by frictional connection or by positive locking connection and no longer jump out of this engagement.

FIGS. 8e, 9d, 10e, 11d, 12d show longitudinal sections of the five design forms in the delivery state and, for the design forms two to five, in each case after a mounting step of the syringe mounting in the autoinjector in a respective position with partially or completely inserted syringe. Moreover, when the syringe is inserted completely, the at least one snapper 4b, which comprises the pull-off cap 4, engages in the gap between the syringe body 13, in particular in its tapering area, and the proximal end of the rigid needle shield 14 (FIGS. 2a, 2b).

The at least one engagement element 1b is shifted together with the syringe holder 1 by a mounting stroke HM, which occurs particularly as last mounting step, axially into the area of the holding section 2b, so that a frictional connection or positive locking connection forms, by means of which it is prevented that the at least one engagement element 1b moves out of the engagement with the tapering section of the syringe body 13 transversely to the longitudinal axis, in particular away from the longitudinal axis L or outward. Moreover, by means of this assembly stroke, the pull-off cap 4 is moved into its distal position, which it assumes in the delivery state of the autoinjector, wherein the pull-off cap 4 is moved by means of at least one snap hook 4a that is braced against the syringe holder 1 by the syringe holder 1.

An embodiment according to the invention of an injection device is represented in FIG. 13. The represented autoinjector 200 corresponds largely to the above-described autoinjector, and reference is made therefore to the above description. Autoinjector 200 comprises a housing 202 that is different from the housing 2. Housing 202 has several fastening points 202f in the shape of indentations. The fastening points 202f are present on both sides on the housing, wherein, in FIG. 13, only one side can be seen. Alternatively, the fastening points 202f could also be configured as axially oriented channels, instead of as point-shaped indentations, without any effect on the inventive idea.

The injection device of this embodiment according to the invention comprises two housing-like shells 230 that are identical (only one of which is represented in FIG. 13). The shells 230 each have an open distal end 230d as well as a proximal end 230e that is shaped to be closed in this embodiment. The shells 230 comprise a plurality of holding devices 230a that are configured as snap arms and on the free end of which a tooth is formed in each case. Moreover, the shells 230 comprise a plurality of blocking devices 230b that are configured as beams or ribs. Both the snap arms 230a and the blocking devices 230b are braced, depending on the position and the associated dimension of the shells 230, by webs 230f or 230g against the shells, wherein the webs 230f or 230 can have variable dimensions, as shown in FIG. 13. For the optimization of the mechanical properties, the shells can comprise additional webs 230h.

The webs 230 are dimensioned in such a manner that they can be snapped on the housing 202. Here, the teeth of the snap arms 230a snap on the indentations of the fastening points 202f. The blocking devices 230b are arranged on the shells 230 in such a manner that, after the shells 230 have snapped on the housing 202, they come to lie axially in each case at the same height as a holding device, lying radially farther outward than the snap arms 230a and thus able to block a radial outward movement of the snap arms 230a. This situation is represented in FIG. 14a. FIG. 14a shows the injection device 200 according to the invention in the assembled state, that is to say after the attachment of the two housing-like shells 230 to the housing 202. For the sake of clarity, the two identical shells 230 are represented in different gray tones. In the state represented in FIG. 14a, the blocking devices 230b block a movement of the snap arms 230a in the arrow direction (see FIG. 14a), that is to say radially outward, thus producing a non-detachable connection between the shells 230 and the housing 202.

An advantageous property of this embodiment is represented in FIG. 14b, wherein the injection device lies on a support, for example, a table 1000. The cross section represented in FIG. 14b shows the oval cross section of the shells 230 and the shaping of the window opening 230c. The represented design here has the advantage that the injection device 200 cannot roll away due to the shaping, as could happen in the case of a circular cylindrical design of the cross section. The elements for the connecting and non-detachable fastening of the shells 230 to the housing 202 are represented again in detail in FIG. 15.

An additional embodiment according to the invention is shown in FIG. 16. The injection device 300 of this embodiment comprises a housing 302, inter alia, on which the fastening points 302f are arranged, which comprise small, tooth-like structures that protrude in the slightly lowered fastening points. Moreover, the injection device of this embodiment comprises two housing-like shells 330. For example, and advantageously, the shells comprise on their outer surface a surface structuring 330i that should allow a reliable gripping for the user. The shells 330 comprise a plurality of holding devices 330a that are configured as arms. At their free end, an opening is arranged in each case. Analogously to the above-described embodiment, the shells 330 each comprise a plurality of blocking devices 330b. When the shells 330 are attached to the housing 302, the arms 330a can snap with the teeth on the fastening points 302f. Analogously to the preceding embodiments, the blocking devices 330b block the disengagement of the arms 330a from snapping on the fastening points. The mechanical properties of the arms 330a can here be varied by dimensioning the ribs 330f.

Figure 17B:
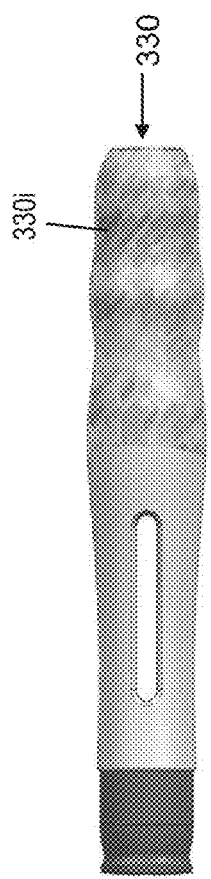
FIGS. 17a-17d: different possible designs of the housing-like shells on the same autoinjector.
Figure 17A:
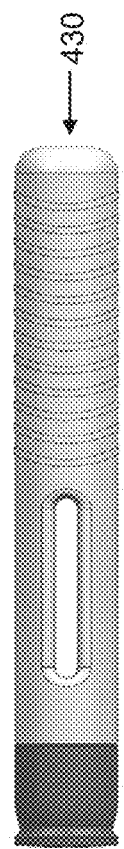
Figure 17D:
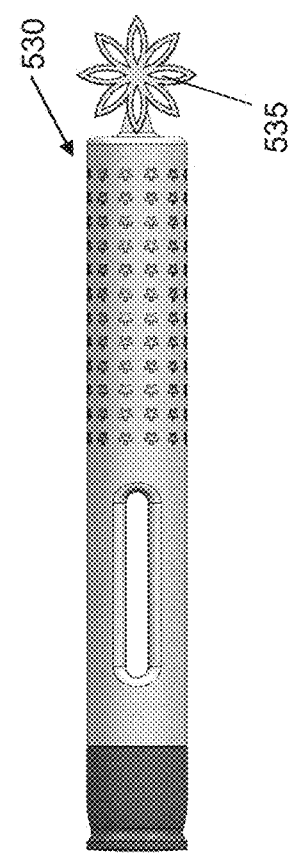
Figure 17C:
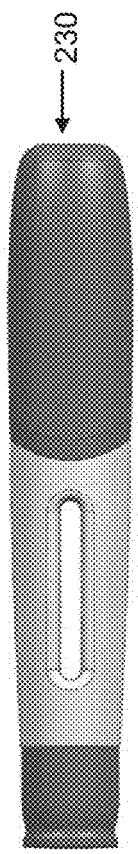

FIGS. 17a-d represent four possible designs of the housing-like shells that are attached to the respective housings. In FIG. 17a, a kind of minimal variant of the shell is represented. Shell 430 has an approximately circular cylindrical shape, wherein shell 430 is a semi-shell. The surface of the shell 430 comprises a surface structuring in the proximal area. In FIG. 17b, an ergonomically shaped variant of a housing-like shell is represented. The shell 330 has a dibble- or dibber-like shape that is also structured in the proximal area 330i. The shell 230 in FIG. 17c has a different external appearance than shell 330; it consists of two material components and was produced in the two-component injection molding process. In the case of shell 230, the proximal portion consists of a softer material than the distal part. The softer material should improve the ease of gripping for the user. Alternative variants for two-component shells can also have, for example, different colors of the two components. FIG. 17d shows a housing-like shell 530 with target group-oriented design adjustment in the form of decorative stars. The structure designed as a large star 535 at the proximal end of the injection device can also have other shapes. For example, palpable symbols can be used, which facilitate or even allow the identification of the injection device by users with impaired vision.

Figure 18B:
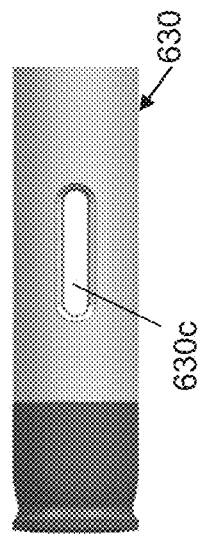
FIGS. 18a-18b: variants of the housing-like shells.
Figure 18A:
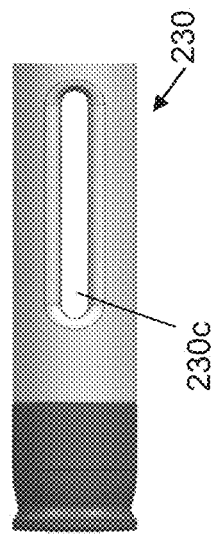

In FIGS. 18a-b, additional advantageous design possibilities of the housing-like shells are represented. Thus, in the example of FIG. 18a, the window opening 230c of the housing-like shells 230 has approximately the same length as the opening 202h of the housing that is located beneath. The opening 202h makes it possible to view the product container 13 and its filling level. In the example of FIG. 18a, the window opening 230c allows approximately the same viewing area as the opening 202h. In the example of FIG. 18b, the window opening 630c of the housing-like shells 230 is clearly shorter, so that only a section of the opening 202h is made visible to the eye of the user. This variant of the housing-like shell can be advantageous, for example, if the product container 13 of the injection device 2 is filled intentionally only with portions of the possible maximum filling quantity. Thus, the same housing 202 can be used for different filling quantities, without giving the user the impression that the product container is insufficiently filled.

Figure 19:
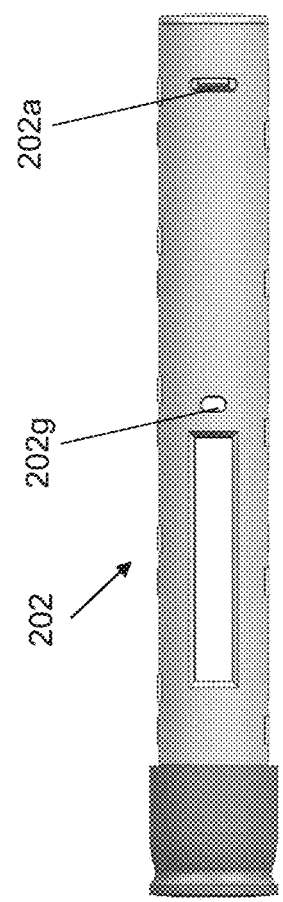
FIG. 19: view of the housing from FIG. 13.
Figure 22:
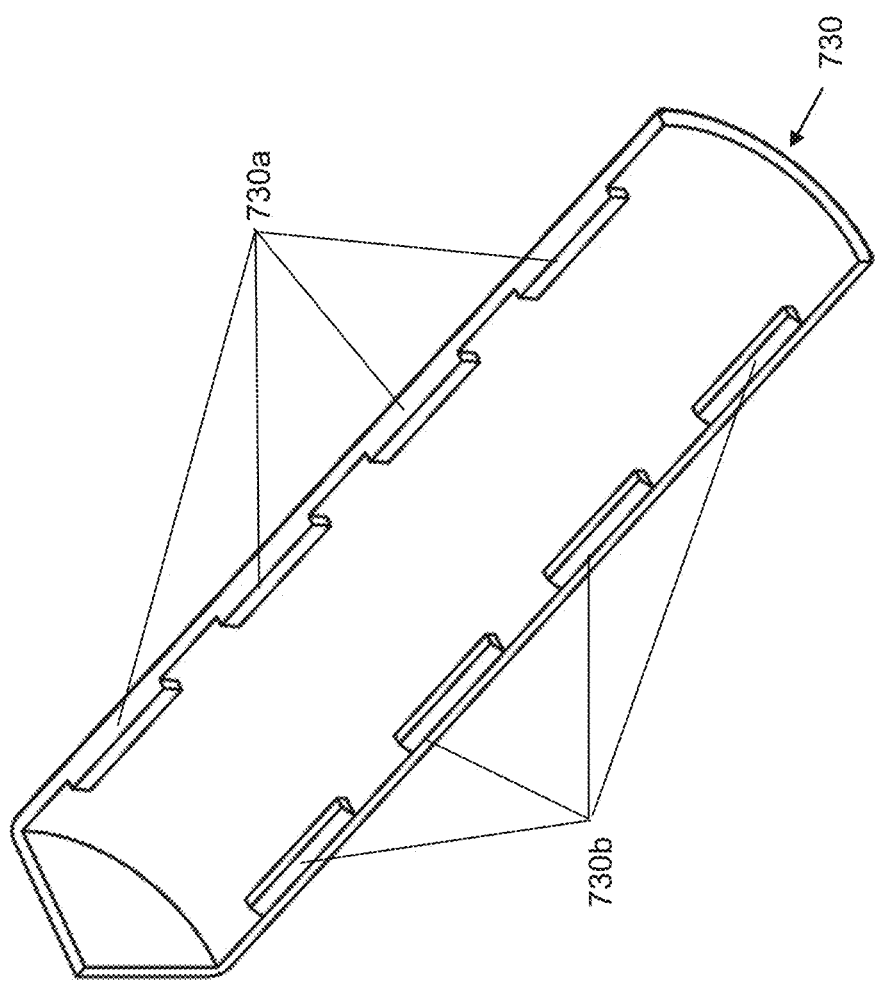
FIG. 22: three-dimensional view of a housing-like shell from FIGS. 20a-21b.
Figure 23C:
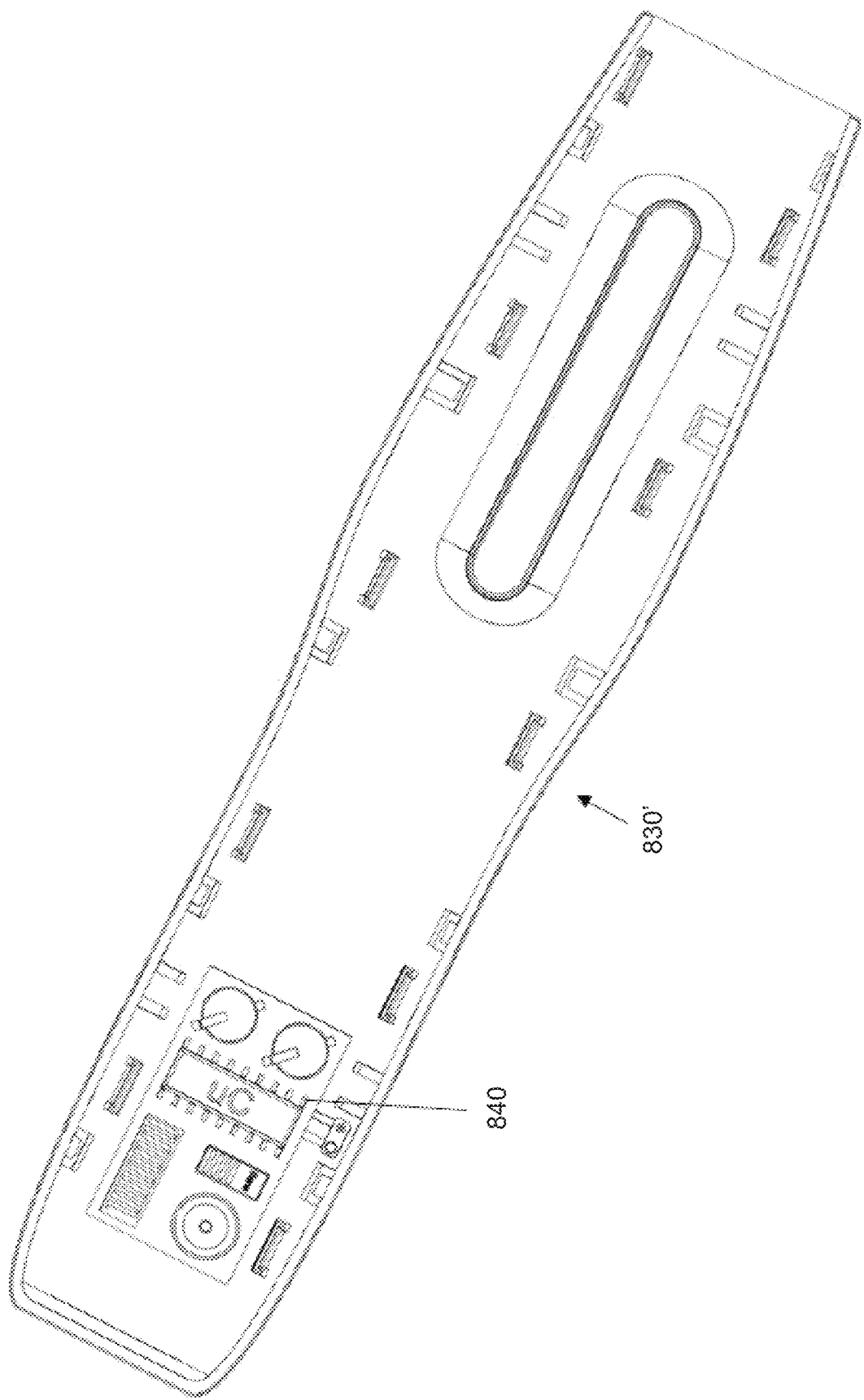
Figure 23E:
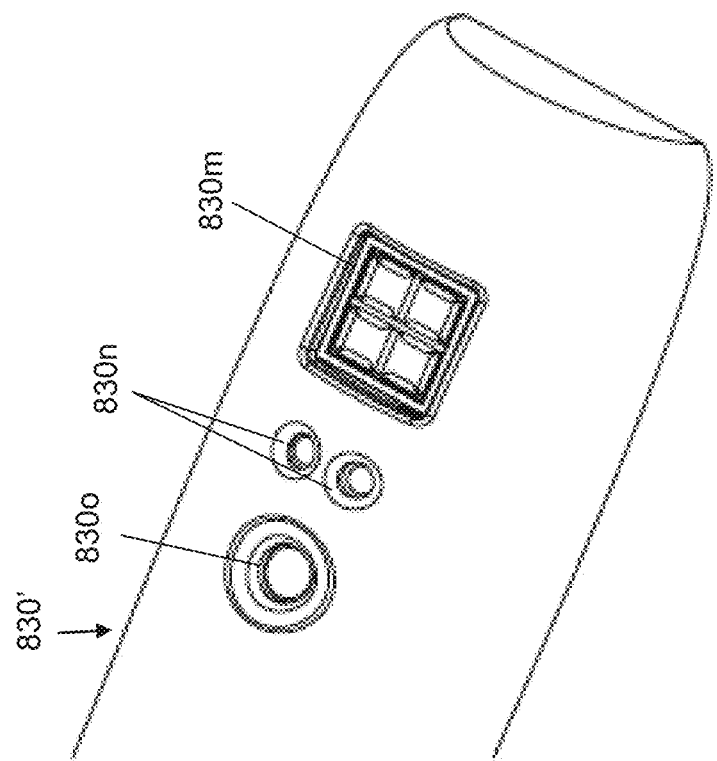
Figure 23D:
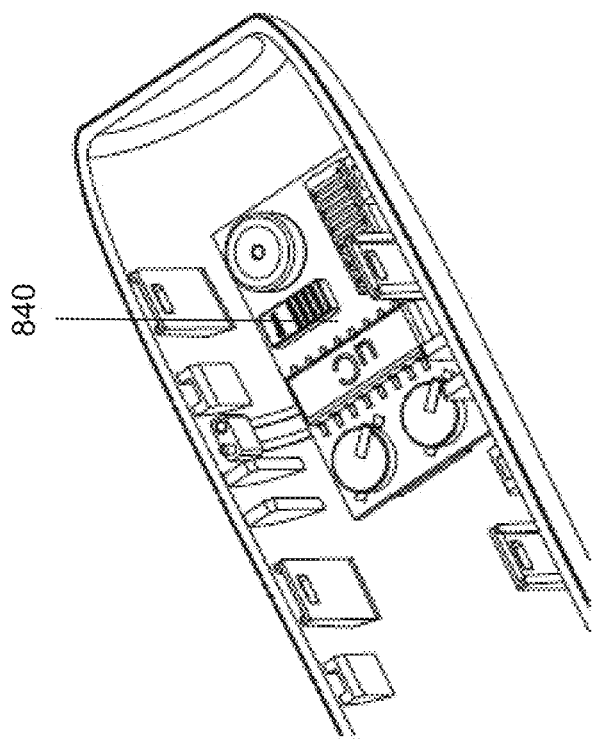

In FIG. 19, the housing 202 is represented again. Here, in FIG. 19, the housing openings 202a and 202g are visible. These openings can be, for example, mounting aids or securing arrangements for mechanical parts, parts of the product container holder, pushbutton openings, sensor openings, light conductor accesses, transparent areas, or accesses for electric contacts. These openings do not have to be visible to the person for him/her to be able to use the injection device. On the contrary, such openings can confuse the user or even mislead to erroneous manipulations, wherefore the housing-like shells advantageously cover these openings.

In FIGS. 20a-22, an additional design of the injection device according to the invention is reproduced. This design comprises the injection device 700 represented, for example, as an autoinjector analogous to the autoinjector 200. The injection device 700 comprises a housing 702. On the external surface of the housing 702, a plurality of fastening points 702f (configured as indentations) is arranged.

Moreover, the injection device 700 comprises four identical housing-like shells 730, which can be attached to the housing 702 in a non-detachable manner. For this purpose, the shells 730 in each case comprise a plurality of holding devices 730a as well as in each case a plurality of blocking devices 730b. The shells 730 are configured in this embodiment as cylinder segment shells that cover an angle of approximately 90°, that is to say approximately a fourth of a circle in cross section. In the present embodiment, the shells have approximately half the length of the injection device 700 and are attached in the proximal half of the injection device. All four shells together enclose the proximal portion of the injection device essentially completely. If one imagines a complete cylinder made of four of the shells 730, then the holding devices 730*a* as well as the blocking devices 730*b* are oriented into the cylinder interior in the radial direction and configured as short arms.

The individual shells 730 can be snapped on the housing 702 if the holding devices 730*a* and the blocking devices 730*b* have been correctly oriented beforehand toward the fastening points 702*f*. The arrangement of holding devices 730*a* and blocking devices 730*b* on the shells 730 are here represented in FIG. 22. In each case, they are arranged along a longitudinal edge of a shell; in this example, the holding devices 730*a* are arranged on one side and the blocking devices 730*b* are arranged on the other side.

In order to snap a shell 730 on the housing 702, the outer edges have to be bent slightly outward, so that the arms of holding devices 730*a* and blocking devices 730*b* can slide over the edges 730*l* of the indentations of the fastening points 702*f*. After a shell 730 has been snapped on the housing 702, the next shell 730 can be snapped on the housing 702. Here, the blocking devices 730*b* are introduced at fastening points 702*f*, in which holding devices 730*a* of the preceding shell 730 have already been introduced. In order to simplify the introduction of the blocking devices 730*b*, at the free end of the arms, a bevel 730*k* is produced. If the blocking devices 730*b* are introduced, then it is no longer possible to disengage the holding devices 730*a*. If all four shells 730 are then attached on the surface of the housing 702, i.e., snapped on, then they can consequently no longer be removed from the housing in a non-destructive manner.

FIGS. 20*b* and 20*c* show the injection device 700 according to the invention in a state in which all four shells 730 have been snapped on. The cross section marked in FIG. 20*c* is represented in FIG. 21*a*. FIG. 21*b* shows an enlargement of a fastening point 702*f*, in which a holding device 730*a* and a blocking device 730*b* are attached.

The four housing-like shells 730 are identical in the explained example. In additional designs of the embodiment, the shells can differ, particularly in shape and material. This is possible as long as the holding devices 730*a* and the blocking devices 730*b* continue to be arranged so that they match the fastening points 702*f* of the housing 702 geometrically and in terms of shape.

In FIGS. 23*a* to 24*b*, an additional advantageous design of an injection device according to the invention is represented. The injection device 800 comprises two housing-like shells 830 and 830' which can be attached to the housing 802 and which together approximately cover the housing 802. Analogously to the shells 330, the housing-like shells 830 and 830' are also attached to the housing 802. Here it should be mentioned that the shells 330 would also fit on the housing 802. The shell 830' has the same shape as the shell 830, but it comprises an additional electronics module 840. The electronics module 840 is attached to the inner side of the shell 830', for example, glued or snapped. The shell 830' comprises openings 830*m*, 830*n* and 830*o*, through which elements of the electronics module are visible or accessible from the outside.

FIGS. 24*a* and 24*b* show the details of the electronics module 840 integrated in shell 830'. FIG. 24*a* shows a first side of the electronics module. As central control unit, the microcontroller 840*f* is provided. Said microcontroller controls the additional components. Thus, the electronics module 840 comprises a sensor module 840*i*, which can comprise, for example, temperature sensors, humidity sensors, light sensors, pressure sensors and/or a microphone. Also on this side of the electronics module 840, a loudspeaker or buzzer 840*e* as acoustic emitter is additionally provided, and the communication module 840*j* is provided for wireless communication with external devices. The energy supply is also provided directly on the electronics module 840, for example, in the form of the batteries 840*g*. The rear side of the electronics module is shown in FIG. 24*b*. There, a pushbutton or button 840*d*, two LEDs 840*b* and 840*c* as well as the display 840*a* are arranged. The light emitting diode 840*b* is here implemented as a green LED and the light emitting diode 840*c* is implemented as a red LED, wherein the color scheme could also be different. The display 840*a* is implemented as a simple 7-segment display with two figures. However, a higher resolution LCD or OLED display could also be implemented. Pushbutton 840*d*, the LEDs 840*b* and 840*c* as well as the display 840*a* are accessible from outside or visible through the corresponding openings 830*o*, 830*n* and 830*m* in the shell 830'.

The sensor 840*h* is connected to the electronics module 840. As can be seen in FIGS. 24*a* and 24*b*, the sensor 840*h* comprises a pin 840*k*. This pin 840*k* is movably mounted on the sensor 840*h*. If the shells 830 and 830' are attached to the housing 802, then the pin 840*k* is moved through a rib on the shell 830 (not shown) into the sensor 840*h* and it closes an electrical contact present in the sensor 840*h*. This contact closure is evaluated by the microcontroller 840*f*. In the present example, contact closure means that the injection device including a product container is mounted in a finished state, since the housing-like shells 830 and 830' are the last parts on the injection device. As a result of the contact closure, the microcontroller activates an internal service-life timer as well as the existing sensors 840*i*, in particular an existing temperature sensor. After the expiration of the service-life duration, the service-life timer signals when the injection device should no longer be used, since the expiration date of the drug present in the product container has been reached. Therefore, during the mounting, the timer is programmed specifically for the drug used and for its shelf life. On the one hand, the signaling occurs optically via the red LED 840*c*, which can blink, particularly after the expiration time has been reached, and, on the other hand, the signaling occurs via the loudspeaker 840*e*, which can emit acoustic signals. The mentioned temperature sensor in the sensor 840*i* measures the temperature of the injection device, wherein the corresponding signal is evaluated by the microcontroller 840*f* and stored in an internal storage (not explicitly shown). If the temperature of the injection device exceeds or falls below a predetermined value for a certain duration, it must then be assumed that the drug has been damaged due to the impact, and consequently the microcontroller activates LEDs, loudspeakers and/or the display in order to signal to the outside that the injection device should no longer be used. Here, the emitted signals differ from the signals emitted after the expiration time has been reached.

In the present example, the sensor module 840*i* moreover comprises a microphone, by means of which the microcontroller 840*f* can detect if the injection device 800 is used for an injection. The triggering of the injection device 800 and the associated movements in the discharging mechanism emit a specific acoustic pattern that is recognized by the microcontroller 840*f*. The microcontroller 840*f* is now programmed such that it signals the injection to the user, and said microcontroller subsequently also signals when the injection process is completed (and, for example, when the injection needle can be removed from the tissue). In the present examples, the green LED 840b starts to blink as soon as the microcontroller has recognized the triggering of the injection device, and the optical display can here be supported by acoustical signals from the loudspeaker 840e (or also by a voice output such as: "The injection is taking place, please wait"). At the same time, with the LED, the display 840a is activated and the predetermined duration of the injection is counted down in seconds, to give the user a reference point as to how long the injection process is to continue. When the counter reaches zero, the injection process is completed. The green LED 840b is now no longer blinking but instead emits light continuously as a sign of completion. In the same way, acoustic feedback via the loudspeaker 840e can occur, such as, for example, a voice output "injection process completed." The microcontroller registers and stores the time and date of the injection process.

In addition to the parts of the electronic module 840 that have already been described in detail, the electronics module can optionally comprise a communication module 840j that, via a Bluetooth, WLAN or GSM, can send data from the injection device 800 or receive data or commands from the outside. In the present example, using the communication module 840j and via Bluetooth, the microcontroller 840f can transmit the time and the date of the injection process as well as a unique identifier of the injection device 800 to a smartphone. An associated app of the smartphone can then keep the therapy records. The unique identifier of the injection device makes it possible to draw conclusions regarding the drug, the drug lot, the precise type of injection device as well as the production lot of the injection device. The data collected by the app can then be transmitted to the treating physician, the insurer or to a server via the Internet.

The pushbutton 840d has two functions: on the one hand, by briefly pressing the pushbutton 840d, a service life verification or function control can be carried out. If the pushbutton 840d is pressed briefly, the microcontroller 840f checks on the one hand whether the timer is running, and, on the other hand, whether the sensor 840i yields plausible measured values, in that the microcontroller 840f compares the current measured values against a stored library of measured values. In the event both are the case, the microcontroller 840f issues a corresponding confirmation via the green LED 840b and the loudspeaker 840a. If one of the verifications shows that there is a problem, then the microcontroller issues feedback via the red LED 840c and the loudspeaker. Thus, a user can verify at any time whether or not the injection device is still usable.

Additional advantageous embodiments are directly accessible to the person skilled in the art without any inventive step, in that he/she varies the number of the housing-like shells or the design of the fastening points, of the holding devices and of the blocking devices in the context of the teaching and his/her technical knowledge.

What is claimed is:

1. An apparatus with an injection device for administering a fluid substance allowing for adjusting the injection device, the injection device comprising a device housing which, on an external side thereof, has a plurality of fastening points, the apparatus comprising:
   a plurality of housing-like shells, comprising at least a first housing-like shell and a second housing-like shell, each of the plurality of housing-like shells having at least one holding device through which the plurality of housing-like shells may be attached to the fastening points of the housing and at least one blocking device arranged thereon, whereby upon attaching all of the plurality of housing-like shells to the housing, the blocking devices of the plurality of housing-like shells prevent the disengagement of the plurality of housing-like shells from the housing by blocking detachment of the holding devices from the fastening points;
   at least one of the housing-like shells comprises an electronic assembly comprising: an electronic control unit; and
   an energy storage to supply energy to the electronic assembly for activation;
   whereby attachment of the plurality of housing-like shells to the housing activates the electronic assembly.

2. The apparatus with the injection device according to claim 1, wherein conductive areas on fastening points of two housing-like shells are electrically connected when the shells are applied to the housing causing the energy storage to power the electronic assembly.

3. The apparatus with the injection device according to claim 1, wherein the electronic assembly comprises a timer which is started upon the electronic assembly being activated.

4. The apparatus with the injection device according to claim 3, wherein the timer is set to a time limit corresponding to an expected service lifetime of the injection device.

5. The apparatus with the injection device according to claim 4, further comprising one or both of a display or a communication module operatively connected to the electronic assembly, wherein upon reaching the time limit of the timer one or both of the display or the communication module may be activated for status signaling of the injection device.

6. The apparatus with the injection device according to claim 1, wherein the electronic assembly further comprises a sensor module and a communication circuit or a communication module for communicating with external devices.

7. The apparatus with the injection device according to claim 6, wherein the communication module is a wireless communication module, selected from the group consisting of a WLAN or Bluetooth module or GSM.

8. The apparatus with the injection device according to claim 6, wherein the communication circuit is a RFID or NFC circuit.

9. The apparatus with the injection device according to claim 1, wherein at least one of the housing-like shells comprises an acoustic pattern sensor operatively connected to the electronic assembly.

10. The apparatus with the injection device according to claim 9, wherein the acoustic pattern sensor is a microphone configured to recognize at least one acoustic pattern associated with a discharging mechanism state of an injection device.

11. The apparatus with the injection device according to claim 10, wherein at least one of the housing-like shells comprises a display for signaling at least one discharging mechanism state.

12. The apparatus with the injection device according to claim 9, wherein the acoustic pattern sensor is configured to recognize when the injection device is used for an injection, that the injection device is triggered or that the injection process is completed.

13. The apparatus with the injection device according to claim 9 wherein the acoustic sensor is arranged in a hollow space between the housing and the housing-like shells.

14. The apparatus with the injection device according to claim 1, wherein once the electronic assembly is activated the electronic control unit can use a voice output to provide user instructions.

15. The apparatus with the injection device according to claim 1, wherein at least one housing-like shell comprises an electronic circuit for unlocking of the injection device.

16. The apparatus with the injection device according to claim 15, wherein the electronic circuit comprises communication means for receiving an unlocking command and an electromechanical actuator movably arranged on the shell and acting through an opening in the housing for unlocking of the injection device.

17. The apparatus with the injection device according to claim 1, further comprising a temperature sensor, by which the temperature within the injection device can be monitored by the electronic assembly to determine when the drug could be damaged by thermal impact.

18. A method of adjusting the haptic, ergonomic or other characteristics of an injection device for administering a fluid substance, said device comprising a housing which, on an external side thereof, has a plurality of fastening points, the method comprising:

providing a plurality of housing-like shells including at least a first housing-like shell and a second housing like shell, each of the plurality of housing-like shells having at least one holding device through which the plurality of housing-like shells may be attached to the fastening points of the housing and at least one blocking device arranged thereon;

attaching all of the plurality of housing-like shells to the housing such that the blocking devices of the plurality of housing-like shells prevent the disengagement of the plurality of housing-like shells from the housing by blocking detachment of the holding devices from the fastening points;

in at least one of the housing-like shells providing an electronic assembly comprising: an electronic control unit comprising at least one of a sensor module and a communications module;

an energy storage to supply power to the electronic assembly, whereby attachment of the plurality of housing-like shells to the housing activates the electronic assembly, where the electronic control unit is powered by the energy storage.

19. The method of claim 18, wherein conductive areas on fastening points of two housing-like shells and in the step of attaching the plurality of housing-like shells to the housing the conductive areas are electrically connected to activate the electronic assembly.

20. The method of claim 18, further comprising providing the electronic control unit with an acoustic pattern sensor configured to recognize at least one acoustic pattern associated with a discharging mechanism state of the injection device.

* * * * *